United States Patent [19]
Saaski et al.

[11] Patent Number: 5,606,170
[45] Date of Patent: Feb. 25, 1997

[54] MULTIFUNCTIONAL SENSOR SYSTEM

[75] Inventors: Elric W. Saaski, Bothell, Wash.; David A. McCrae, Richmond, Calif.

[73] Assignee: Research International, Inc., Woodinville, Wash.

[21] Appl. No.: 383,362

[22] Filed: Feb. 3, 1995

[51] Int. Cl.$^6$ .......................... G01N 21/01; G01N 21/25; G01N 21/62
[52] U.S. Cl. ................... 250/458.1; 250/227.14
[58] Field of Search ................. 250/458.1, 337, 250/474.1, 341.2, 459.1, 227.14, 227.18, 227.32

[56] References Cited

U.S. PATENT DOCUMENTS

| | | |
|---|---|---|
| 3,580,082 | 5/1971 | Strack . |
| 3,831,137 | 8/1974 | Cuomo . |
| 4,158,310 | 6/1979 | Ho . |
| 4,447,546 | 5/1984 | Hirschfeld . |
| 4,558,014 | 12/1985 | Hirschfeld et al. . |
| 4,582,809 | 4/1986 | Block et al. . |
| 4,617,938 | 10/1986 | Cook . |
| 4,654,532 | 3/1987 | Hirshfeld ................. 250/458.1 |
| 4,673,299 | 6/1987 | Dakin ..................... 250/458.1 X |
| 4,678,904 | 7/1987 | Saaski et al. . |
| 4,708,494 | 11/1987 | Kleinerman ............... 250/458.1 X |
| 4,716,121 | 12/1987 | Block et al. . |
| 4,763,009 | 8/1988 | Février et al. ............ 250/458.1 |
| 4,778,987 | 10/1988 | Saaski et al. . |
| 4,852,967 | 8/1989 | Cook et al. . |
| 4,945,230 | 7/1990 | Saaski et al. . |
| 4,945,245 | 7/1990 | Levin ..................... 250/458.1 X |
| 5,061,857 | 10/1991 | Thompson et al. . |
| 5,152,962 | 10/1992 | Lackie ................... 250/459.1 X |
| 5,430,813 | 7/1995 | Anderson et al. . |

FOREIGN PATENT DOCUMENTS

| | | | |
|---|---|---|---|
| 53-89793 | 8/1978 | Japan ................ 250/474.1 |
| 59-155775 | 9/1984 | Japan ................ 250/474.1 |
| 9000035 | 1/1990 | WIPO ................ 250/459.1 |

OTHER PUBLICATIONS

Kyuma et al., Development of Fiber Optic Sensing Systems, 1982, Optics and Lasers in Engineering, vol. 3, pp. 155–182. no month.

Krohn, D., Fiber Optic Sensors: IntensityModulation, Jan. 1987, Photonics Spectra, pp. 59–70.

Dandridge, A., Fiber-Optic Sensors Make Waves in Acoustics, etc. Nov. 1990, Circuits and Devices, pp. 13–19.

He, et al., Diaphragm Size and Sesnitivity for Fiber Optic Pressure Sensors, 1991, Fiber Optic & Laser Sensors IX, pp. 152–156. no month.

(List continued on next page.)

*Primary Examiner*—Edward J. Glick
*Attorney, Agent, or Firm*—Gregory W. Moravan

[57] ABSTRACT

A multifunctional sensor system for an intrinsic type optical sensing fiber. A numerical aperture controlling optical input element for the excitation fiber may maximize the amount of sensing fiber modulated return light. The excitation fiber may be centered in a ring or linear array of return fibers, to inject excitation light into the return light poor center of the sensing fiber; and to capture return light from the return light rich outer parts of the sensing fiber. Tipping the return fibers with respect to the sensing fiber may increase their capture of high numerical aperture return light. The sizes and number of the adjacent ends of the excitation, return and sensing fibers may be selected to minimize the effects of any lateral displacement between the adjacent ends. The sensing fiber may generate both reference and sensor return light; and a ratiometric output signal may be derived from the reference and sensor return light which may be free of certain system errors. Ribbon-like sensor and sensing fibers may be provided; along with a transition fiber if the sensor and sensing fibers are of different sizes. An annular, possibly tapered, waveguide may be provided around the sensing fiber, to better capture the return light. The waveguide may either pass the target objective; or it may be hollow, and define a sample chamber for the target objective. The ends of the sensing fiber and/or the annular waveguide may be mirrored, to dramatically increase the output of return light, and thus, the sensitivity of the sensor system.

33 Claims, 11 Drawing Sheets

OTHER PUBLICATIONS

Scheper, et al., A Fiber Optic Biosensor, etc., 1990, Biosensors & Bioelectronics, pp. 125–135. no month.

Glass et al., Effect of Numerical Aperature on Signal Level etc., Jun 1987, Applied Optics, vol. 26, No. 11, pp. 2181–2187.

Ratner, V., Calculation of the Angular Distribution and Waveguide, etc., 1994, Sensors and Actuators B, vol. 17, pp. 113–119. no month.

Saaski et al., Thin–Film Fabry Perot Temperature Sensors, 1992, no month Temperature, Its Measurement and Control, etc., vol. 6, Part 2, pp. 731–734.

Sepaniak et al., Design Consideration for Anti–body Based, etc., 1989, Antibody Based Fiber–Optic Chemical Sensors, pp. 318–330. no month.

Astles, et al., Reversible Fiber–Optic Immunosensor Measurements, 1993, Sensors and Actuators B, vol. 11, pp. 73–78. no month.

Zhu et al., Determination of the Effective Depth for Double Fiber, etc., 1992, Applied Spectroscopy, vol. 46, No. 6, pp. 919–924. no month.

Vo–Dinh et al., Development of Fiber–Optic Immunosensors etc., 1992, Pollution Prevention in Industrial Processes, Chapt. 22, pp. 270–283. no month.

Wong et al., Reusable Fiber–Optic–Based Immunosensor etc., 1993, Analytica Chimica Acta, vol. 279, pp. 141–147. no month.

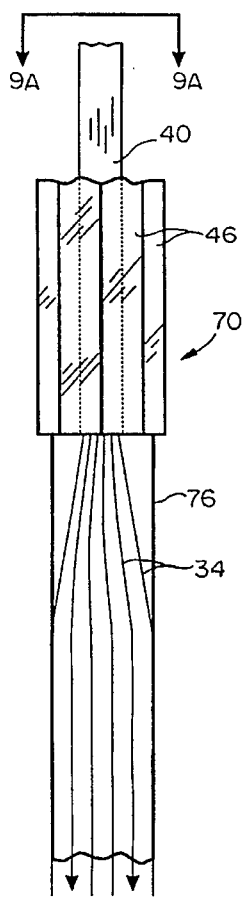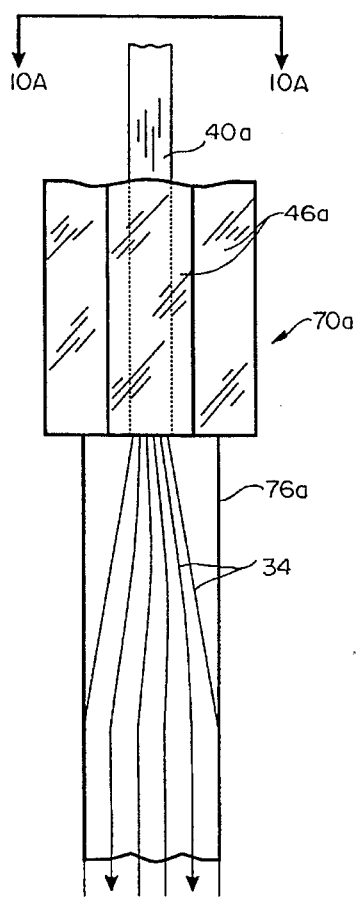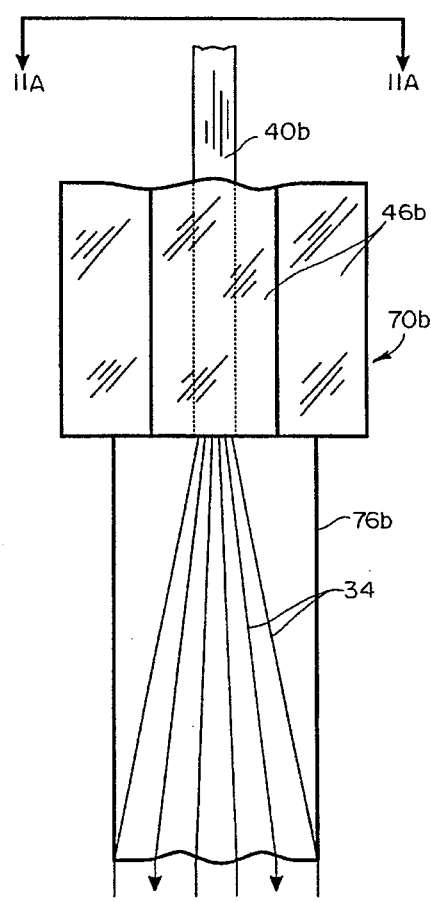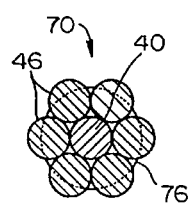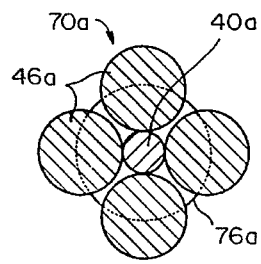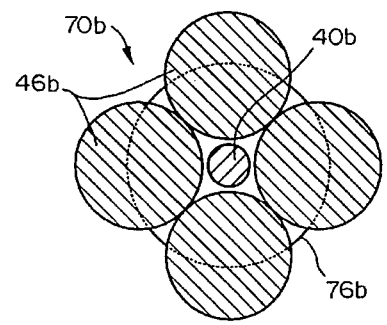

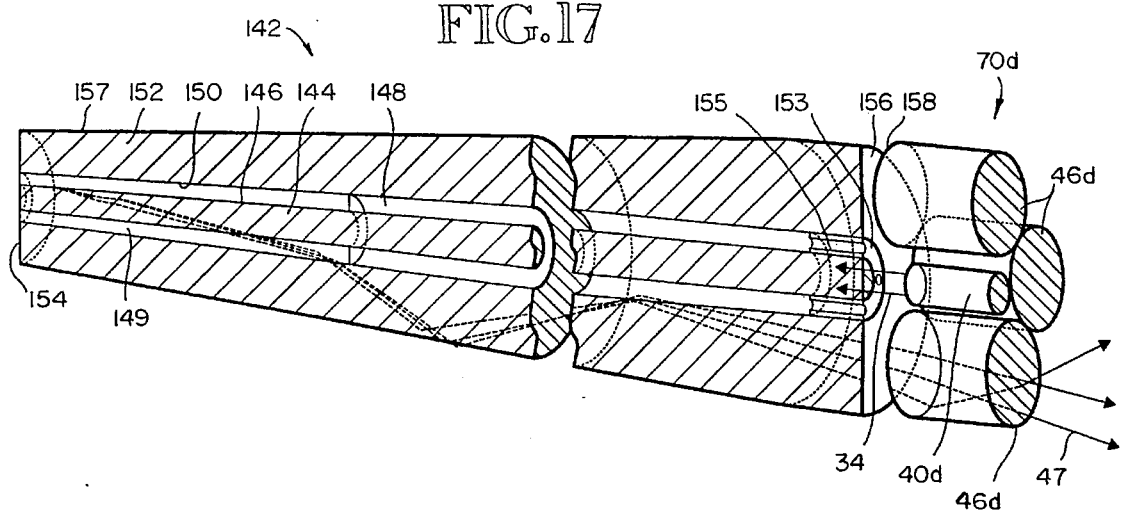
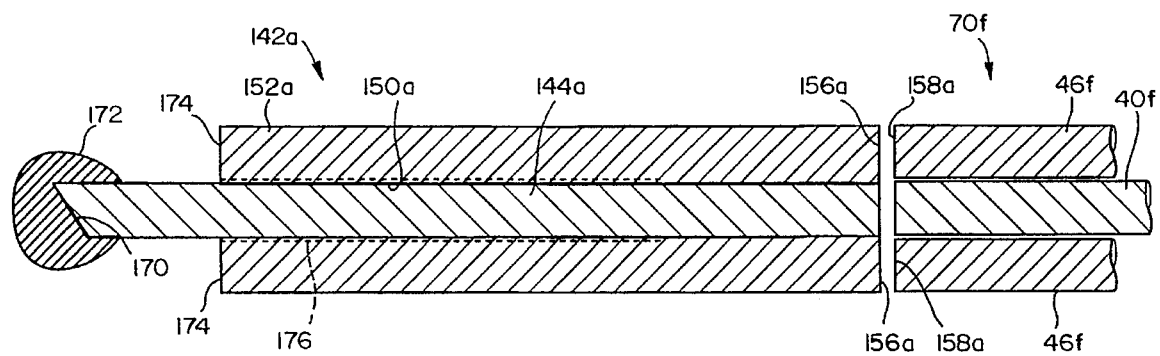

MULTIFUNCTIONAL SENSOR SYSTEM

BACKGROUND OF THE INVENTION

The present invention relates to sensor systems. More particularly it relates to a multifunctional sensor system which may include an intrinsic optical fiber sensor interrogated by modally controlled excitation light carried by an excitation optical fiber, wherein the sensor system may capture the sensor modulated return light with an array of return light optical fibers.

SUMMARY OF THE INVENTION

An intrinsic optical fiber sensor is one having an intrinsic optical sensing fiber which directly interacts with its surroundings to act as a signal transduction device; wherein the intrinsic sensing fiber carries both excitation (input) light, and sensor modulated return (output) light.

One aspect of the present invention may be to provide a multifunctional sensor system having an intrinsic optical fiber sensor, in which the modality of the excitation light is controlled in order to optimize the ability of the excitation light to stimulate the sensor's intrinsic sensing fiber. Such modality control may be particularly valuable where the intrinsic sensing fiber detects the target chemical or the target physical parameter by the interaction of the excitation light with the sensing fiber's outer surface, or with a coating on the sensing fiber's outer surface.

A further aspect of the present invention may be to control the modality of the excitation light by use of optical means, such as by use of a conical tip or pit on the input end of the excitation optical fiber which delivers the excitation light to the sensor's intrinsic sensing fiber. Such a conical tip or pit may cause the excitation light which is injected into the excitation fiber to travel in paths which are less coaxially aligned with the excitation fiber's longitudinal axis than might otherwise be the case. In other words, the conical tip or pit may be selected to maximize the number of internal reflections, or bounces, of the excitation light within the excitation fiber (and thus, within the sensor's intrinsic sensing fiber), per unit length, than might otherwise be the case.

Another aspect of the present invention may be to provide an optical fiber bundle which both delivers excitation light to the sensor's intrinsic sensing fiber, and receives sensor modulated return light from the sensor's intrinsic sensing fiber.

Such an optical fiber bundle may comprise at least one, centrally located, excitation optical fiber, for optimizing the injection of the excitation light into the central, return light poor portion of the sensor's intrinsic sensing fiber.

Such an optical fiber bundle may further comprise an array of return light optical fibers positioned in an annular ring or a linear arrangement with respect to the excitation fiber, for optimizing the reception of sensor modulated return light from the return light rich portions of the sensor's intrinsic sensing fiber.

The sizes of the excitation optical fiber's output end, the return light optical fibers' input ends, and the sensing fiber's interface end may be selected to minimize the effect of lateral displacements of their ends with respect to each other.

A further aspect of the present invention may be to tip at least some of the array of return light optical fibers at an angle with respect to the longitudinal axis of the sensor's intrinsic sensing fiber, to help maximize the ability of the return fibers to capture and carry any sensor modulated return light which may have a high numerical aperture (NA).

Another aspect of the present invention may be to provide the multifunctional sensor system's photodiode receiver module with at least two different wave bands of light from the sensor's intrinsic sensing fiber; namely, a sensor wave band of light (which carries information about the sensed target chemical or target physical parameter), and a reference wave band of light; wherein both of such wave bands have travelled at least substantially the same optical path from the sensor to the receiver module.

Such a reference wave band of light may comprise either a reference portion of the excitation light which has been reflected or refracted back from the sensor's intrinsic sensing fiber; or it may comprise reference fluorescence light which has been emitted by the sensor's intrinsic sensing fiber (or by a fluorescent coating on outer surface of the sensor's intrinsic sensing fiber), under the stimulation of the excitation light.

Further aspects of the present invention may be to provide the photodiode receiver module with means for dividing the light it receives from the sensor into a sensor wave band and a reference wave band; and to further provide the receiver module with means for generating sensor electrical signals and reference electrical signals from those two wave bands, respectively.

Another aspect of the present invention may be to provide the photodiode receiver module with means for taking the ratio of the sensor and reference electrical signals, to provide a ratiometric output electrical signal in which certain errors of the multifunctional sensor system have been reduced, or even nulled.

A further aspect of the present invention may be to provide an improved intrinsic optical sensor which may capture more of the sensor modulated return light generated by the sensor's intrinsic sensing fiber, for greater sensitivity, than may be the case with conventional intrinsic optical sensors.

One form of such an improved intrinsic optical sensor may comprise a ribbon-like intrinsic optical sensing fiber. Such an optical sensor may further comprise a ribbon-like sensor fiber having a cross-sectional larger than that of the ribbon-like sensing fiber, and a transition fiber connecting such ribbon-like sensor and sensing fibers. With such a ribbon-like sensing fiber, the excitation fiber and the array of return light fibers may be positioned in a linear arrangement, with the excitation fiber being located in the central portion of the linear arrangement.

Another form of such an improved intrinsic optical sensor may comprise an annular, hollow waveguide which may surround a cylindrical intrinsic sensing fiber, wherein such annular, hollow waveguide may provide for improved capture of the sensor modulated return light emitted by the intrinsic sensing fiber. For the purposes of the present invention, such an improved sensor will be termed an intrinsic optical sensor having an intrinsic optical sensing fiber, even though the improved sensor's intrinsic sensing fiber may carry little, or none, of the sensor modulated return light.

In such an improved intrinsic optical sensor, the distal end of the sensing fiber may be mirrored, to increase the amount of sensor modulated return light generated by the sensing fiber. In such an improved intrinsic optical sensor, the distal end of the annular waveguide may be silvered to increase the amount of sensor modulated return light transmitted by the annular waveguide to the optical receiver module.

The improved sensor's annular, hollow waveguide may serve the dual functions of not only acting as a waveguide for the sensor and reference wave bands of light generated by the sensor's intrinsic sensing fiber; but it may also serve as the outer wall of the target chemical sample chamber which may surround the sensor's sensing fiber.

Alternatively, the target chemical sample chamber may be eliminated; the annular, waveguide may be sized to snugly surround, or coat, the sensor's intrinsic sensing fiber; and the waveguide may be made of a material selected to permit the target chemical to reach the intrinsic sensing fiber when the waveguide's external surface is exposed to the target chemical. Such an annular waveguide may comprise an annular sensor fiber, an annular transition fiber, and an annular portion which surrounds the sensor's sensing fiber. The annular sensor fiber may have a cross-sectional area larger than that of the annular portion which surrounds the sensing fiber. The transition fiber may optically connect the annular sensor fiber with the annular portion which surrounds the sensing fiber.

A further aspect of the present invention may be to use an optical fiber bundle, similar to those described above, to deliver excitation light to, and to convey sensor modulated return light from, such an improved sensor having an annular, hollow waveguide.

Such an optical fiber bundle may be arranged so that the delivery of the excitation light to the improved sensor's central, intrinsic sensing fiber may be maximized by centrally aligning the fiber bundle's excitation fiber with the intrinsic sensing fiber.

Such an optical fiber bundle may also be arranged so that the delivery of the sensor modulated return light from the improved sensor's annular, hollow waveguide to an annular array of return light fibers may be maximized by appropriately sizing and locating the annular array of return light fibers so that their input ends are adjacent to the annular output end of the annular, hollow waveguide.

It should be understood that the foregoing summary of the present invention does not set forth all of its features, advantages, characteristics, structures, methods and/or processes; since these and further features, advantages, characteristics, structures, methods and/or processes of the present invention will be expressly or inherently disclosed to those skilled in the art to which it pertains by all of the disclosures herein.

BRIEF DESCRIPTION OF THE FIGURES

FIG. 9 is a diagrammatic top elevational view of the interface between a first embodiment of the sensor connector's sensor optical fiber, and a first embodiment of the sensor interface connector's optical fiber bundle comprising an excitation fiber and an array of return light fibers;

FIG. 9A is a cross-sectional view, taken along line 9A—9A of FIG. 9;

FIG. 10 is a diagrammatic top elevational view of the interface between a second embodiment of the sensor connector's sensor optical fiber, and a second embodiment of the sensor interface connector's optical fiber bundle comprising an excitation fiber and an array of return light fibers;

FIG. 10A is a cross-sectional view, taken along line 10A—10A of FIG. 10;

FIG. 11 is a diagrammatic top elevational view of the interface between a third embodiment of the sensor connector's sensor optical fiber, and a third embodiment of the sensor interface connector's optical fiber bundle comprising an excitation fiber and an array of return light fibers;

FIG. 11A is a cross-sectional view, taken along line 11A—11A of FIG. 11;

FIG. 17 is an enlarged, perspective view of the tapered annular waveguide embodiment of the optical sensor of the present invention, shown partly in cross-section, and partially exploded, along with its associated optical fiber bundle comprising an excitation fiber and an array of return light fibers;

FIG. 17A is longitudinal cross-sectional view of another embodiment of the annular waveguide optical sensor of the present invention;

DESCRIPTION OF THE PREFERRED EMBODIMENTS

Figure 1:
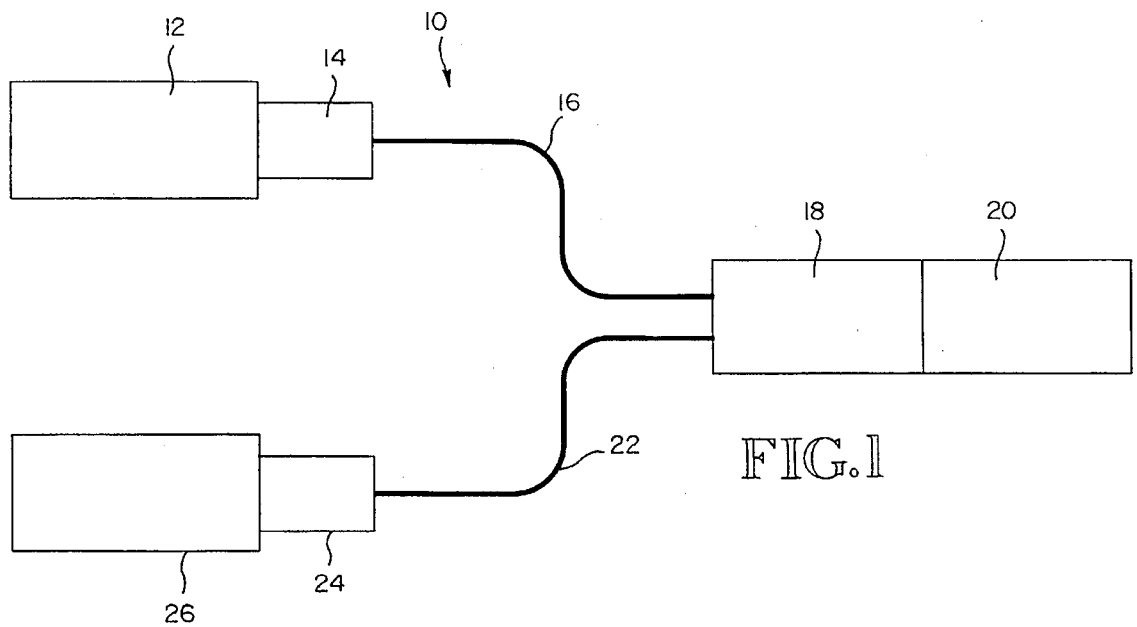
FIG. 1 is a diagrammatic view of the multifunctional sensor system of the present invention.

Turning now to FIG. 1, the multifunctional sensor system 10 of the present invention may comprise eight main components, namely a light transmitter module 12, a transmitter connector 14, an excitation optical fiber cable 16, a sensor interface connector 18, an optical sensor 20, a return light optical fiber array cable 22, a receiver connector 24, and a light receiver module 26.

In general, during operation, excitation light from the transmitter module 12 may pass sequentially through the transmitter connector 14, the excitation optical cable 16, and the sensor interface connector 18 to the sensor 20; which may then modulate the excitation light in some fashion, as a function of the sensed target chemical or target physical parameter.

The sensor modulated return light from the sensor 20 may then pass sequentially through the sensor interface connector 18, the return optical cable 22, and the receiver connector 24 to the light receiver module 26; which may then produce one or more electrical output signals as a function of the sensed target chemical or target physical parameter.

The optical sensor 20 may be any suitable conventional intrinsic optical sensor, i.e., an optical sensor which may detect target chemicals or target physical parameters by the use of an intrinsic optical sensing fiber which interacts directly with its surroundings. Alternatively, the sensor 20 may be the novel intrinsic sensors 142, 142a, or 142b illustrated in FIGS. 17, 17A and 17B, respectively, or the sensor 20 may be the novel intrinsic sensor 200 illustrated in FIGS. 18–20; all of which will be described in detail below. In all cases, the intrinsic sensing fiber of the sensors 20, 142,142a, 142b, 200 may not only serve as a signal transduction device; but they may also serve to convey and/or modify in angle and/or position the excitation (input) light, and/or the sensor modulated return (output) light.

The intrinsic sensing fiber may interact with its surroundings in any conventional way such as, for example, by changing its optical transparency; by changing its spectral properties; by converting light energy of one wavelength to another, as through fluorescence; by changing its surface, bulk, or other physical properties; and/or by changing its chemical properties.

For example, a typical suitable conventional intrinsic optical sensor 20 may be a fluorescence light-generating type of intrinsic sensor, which uses conventional so-called evanescent wave excitation techniques, and which detects low levels of target chemicals by using fluorescence-based immunoassay techniques.

In such a sensor 20, the outer surface of a portion of its intrinsic sensing fiber may be coated with a longitudinally extended, thin, annular layer of fluorophore(s) which are modulated in fluorescence output by the target chemical while being stimulated by suitable evanescent wave excitation light 34 traveling in its sensing fiber. Such fluorescence may be of an intensity which is a function of the concentration of the target chemical.

Conventional evanescent wave detection techniques utilize the fact that at any reflective surface the electromagnetic waves of the excitation light 34 actually penetrate into the medium backing the reflective surface a short distance—typically about b $\frac{1}{10}$ of a wavelength of the excitation light 34. For example, if the intrinsic optical sensor 20 just described above is immersed in a liquid containing the target chemical, the molecules of fluorophore(s) on its sensing fiber's outer surface will, when in the presence of the target chemical, be modulated in fluorescence output when stimulated by the evanescent waves of the excitation light 34 which penetrate the outer surface of its sensing fiber.

One advantage to such an evanescent wave detection technique may be that such a sensor 20 will show considerable insensitivity to dirt particles in the fluid being tested, since the distance the evanescent waves penetrate outside the sensing fiber is so small. Another advantage may be that the sensitivity of the sensor 20 may be increased, within limits, by simply increasing the length of its sensing fiber.

On the other hand, one disadvantage of an evanescent wave detection technique may be that, even under the best of conditions, the fluorescence generated by the fluorophore(s) on the sensing fiber's outer surface may be of a comparatively low intensity. This may be because much of the excitation light traversing the sensing fiber's length may make only a few reflections with the sensing fiber's sidewalls, and it is only at such reflections that the needed evanescent waves are generated. Thus, it may be desirable to find ways, such as those described herein, to make the excitation light reflect off from the sensing fiber's sidewalls more frequently (generate higher NAs), in order to increase the degree of evanescent interrogation of the fluorophore(s) on the sensing fiber's outer surface.

In the discussion of the multifunctional sensor system 10 of the present invention which follows, the intrinsic optical sensor 20 will be described, by way of non-limiting example, as a fluorescence light-generating type of intrinsic optical sensor 20 of the kind described above which is excited by evanescent waves; wherein the sensor 20 is being used to detect a target chemical. However, the optical sensor 20 may be any other suitable type of conventional intrinsic optical sensor, and may be used to detect a target physical parameter. In addition, for clarity and simplicity the diameters given, by way of example, for any of the optical fibers in the sensor system 10 will be the diameters of their light conveying cores; and will not include the thickness of any cladding or coating normally found on most optical fibers.

Figure 2:
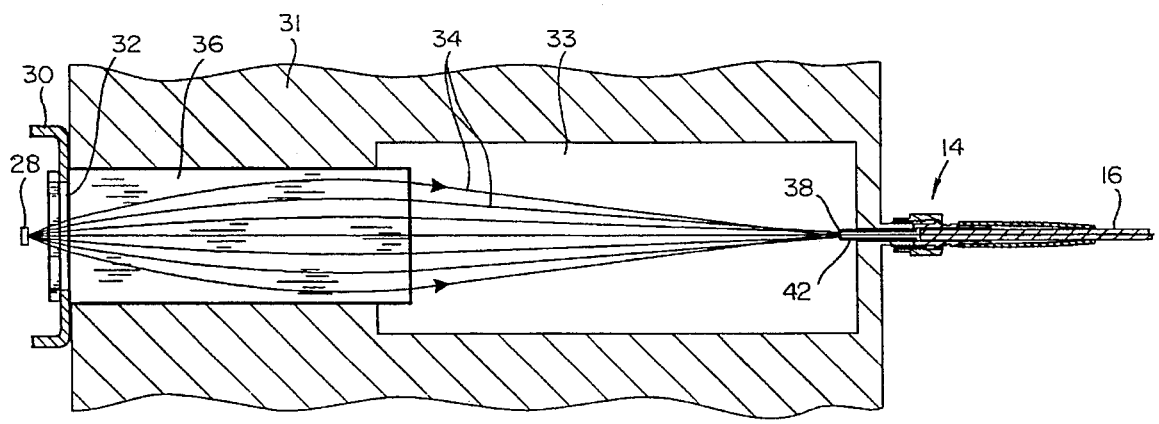
FIG. 2 is an enlarged, fragmentary, elevational view of the present invention, partly in longitudinal cross-section, showing a portion of its light transmitter module, as well as the transmitter connector between the transmitter module and the excitation optical fiber cable.
Figure 2A:
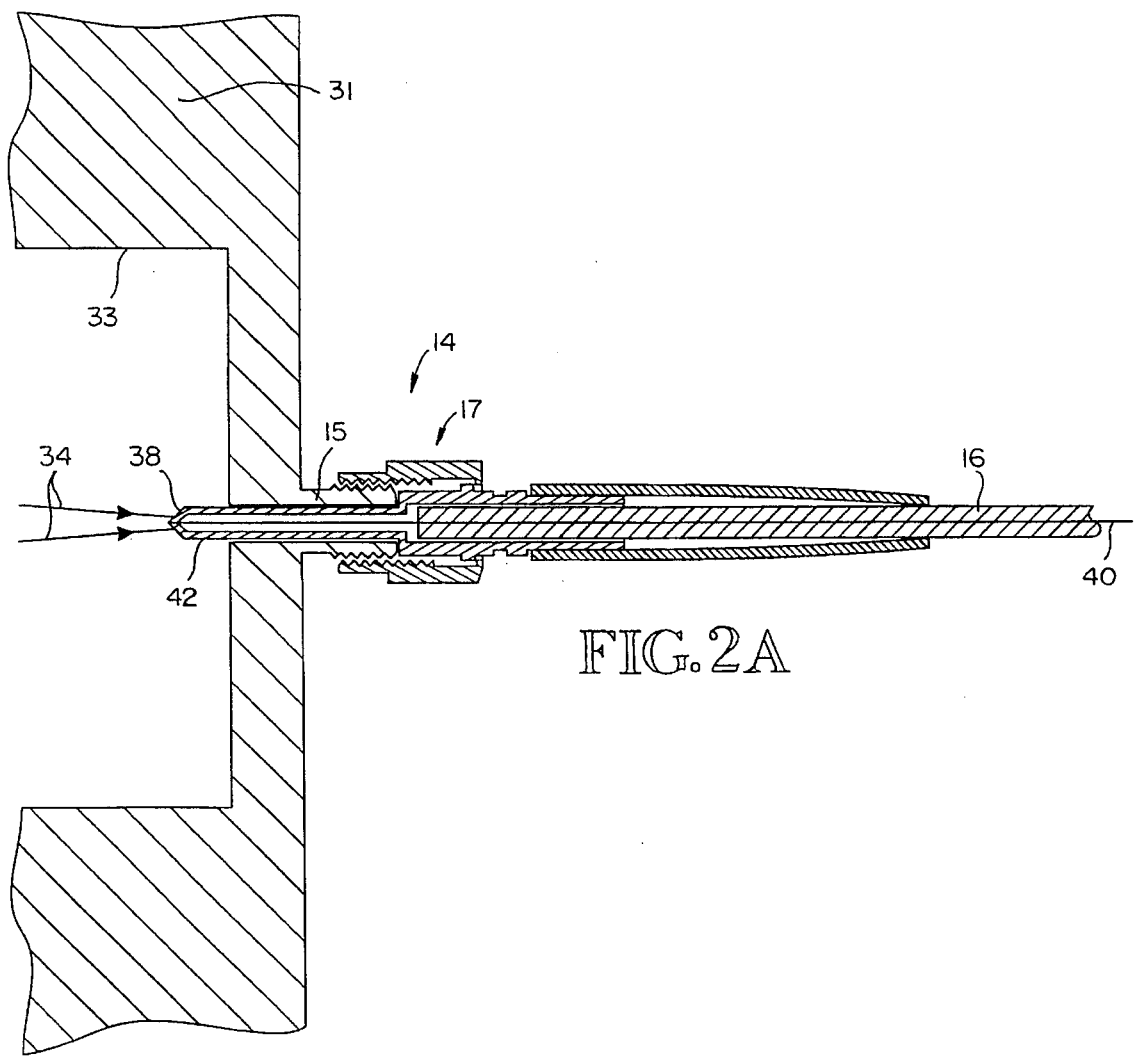
FIG. 2A is an enlarged view of the right side of FIG. 2.

Turning now to FIGS. 2 and 2A, the light transmitter module 12 may comprise a conventional light source 28 located within a housing 30 having a window 32. The light source 28 may be, for example, a model DL-3038-011 laser diode, manufactured by the Sanyo Company located in Tottori, Japan, which emits 5 Mw of light at 635 nm, although any other suitable source of laser light may be used. Alternatively, a non-laser light source 28 may be used.

The excitation light 34 from the light source 28 may be magnified and focused by any suitable conventional means, such by use of a 0.25 pitch graded refractive index (GRIN) lens 36, having a 3 mm diameter. A suitable GRIN lens may be a type SLW unit manufactured by NSG America located in Somerset, N.J.

GRIN lenses may be preferred because they may be selected to accept light over a wide light source 28 output angle. GRIN lenses may also be preferred because they may be selected to have a compact size and a short focal length, which may result in a more compact transmitter module 12 than might otherwise be the case.

Alternatively, the lens 36 may be any other type of suitable lens, such as a ball lens, an aspherical lens, or a multi-element conventional lens train.

As illustrated in FIGS. 2 and 2A, the lens 36 may be selected to magnify the excitation light 34 from the light source 28 so that an image of the light source 28 may be projected onto the end 38 of the excitation optical fiber 40 in the connector pin 42 of the transmitter connector 14. It may be desirable that the image be approximately equal in size to the fiber 40's input diameter, and that the excitation light rays 34 subtend a small total angle. Since solid state laser diodes have very small emitter areas, large magnifications of 10×, or more, may be not only practical, but desirable.

This may be because at large magnification ratios, the excitation light rays 34 entering the excitation fiber 40 are more nearly parallel to the fiber 40's longitudinal axis, allowing the rays 34 to be more nearly approximated as entering the fiber 40 at a small angle. This may allow greater manipulation of the excitation light 34's modal characteristics within the fiber 40 and sensor 20 than might otherwise be the case, as will be described subsequently.

The excitation cable 16, which carries the excitation fiber 40, may be any suitable conventional optical fiber cable.

The excitation fiber 40 may be any suitable step index or graded index optical fiber constructed from glass, plastic or plastic/glass that has an effective diameter, such as 200–250 microns, which is compatible with the diameter of the sensor optical fiber 76 at the sensor connector 72's pin 140, as will be described in more detail subsequently.

A spacing block 31, having a cavity 33, may be provided between the housing 30 and the transmitter connector 14, to mount the lens 36 and the transmitter connector 14; and to provide appropriate spacing therebetween, for proper focusing of the excitation light 34 from the lens 36 onto the end 38 of the excitation fiber 40.

The transmitter connector 14 may be any suitable conventional optical connector, such as an SMA (Small Mechanical Adapter) connector; and may have a male portion 15 mounted to the spacing block 31; and a female portion 17, which carries the excitation optical fiber 40. For simplicity and clarity, the mechanical details and operation of the SMA connector 14 illustrated in FIG. 2A will not be described, since they are all conventional and well known in the art.

Figure 3:
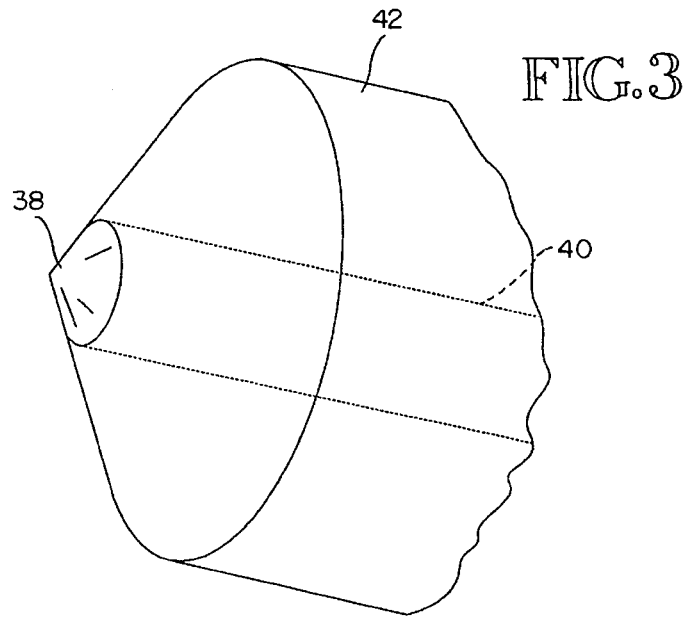
FIG. 3 is an enlarged perspective view of the transmitter end of the connector pin in the transmitter connector.

One important aspect of the present invention may be that, as best seen in FIG. 3, the end 38 of the excitation fiber 40 (and coincidentally, the tip of the connector pin 42 which supports it), may be ground and polished to produce a conical end surface.

The conical end 38 of the excitation fiber 40 may be important since it may cause the excitation light 34 launched into it from the lens 36 to be refracted symmetrically outwardly from the longitudinal axis of the excitation fiber 40. This may result in the excitation light rays 34, which travel down the excitation fiber 40, being less coaxially aligned with the excitation fiber 40's longitudinal axis, than would otherwise be the case.

This may be of substantial value if the optical sensor 20 is an evanescent wave excited, fluorescence light-generating type of intrinsic sensor, of the kind described above. As will be recalled, during operation of such an evanescent wave excited, fluorescence light-generating type of intrinsic sensor 20, the excitation light 34 may interact with the longitudinally extended, thin, annular layer of fluorophore(s) on its intrinsic sensing fiber, to produce fluorescence light (the sensor modulated return light 47), of an intensity which may be a function of the concentration of the target chemical which is being detected.

Thus, for such an evanescent wave excited, fluorescence light-generating type of intrinsic sensor 20, it may be desirable to launch the excitation light 34 into the excitation fiber 40 at the highest possible angle which is less than the angle at which the excitation light 34 will be lost from the excitation optical fiber 40. This may be done in order to help maximize the effectiveness with which any given amount of the excitation light 34 will excite the longitudinally extended, thin, annular layer of fluorophore(s) on the sensor 20's sensing fiber.

Such effectiveness may be maximized because, for each unit of length of the longitudinally extended, thin, annular layer of fluorophores, there will be many more bounces of the high angle excitation light 34 within the perimeter of the sensing fiber beneath the layer of fluorophores, as the excitation light 34 travels down the sensing optical fiber; as compared to if the excitation light 34 were travelling more nearly parallel to the longitudinal axis of the sensor 20's sensing fiber.

However, depending on the optics involved, all of the excitation light 34 entering the conical end 38 of the excitation fiber 40 may not make exactly the same angle with respect to the excitation fiber 40's longitudinal axis. Thus, the particular cone half-angle which is selected for the excitation fiber 40's conical tip 38 may be a compromise which, on the average, maximizes the amount of high angle excitation light 34 which is successfully waveguided down the sensing fiber 40 (to thereby maximize its ability to excite the layer of fluorophore(s) on the sensor 20's sensing fiber); while simultaneously minimizing the amount of the excitation light 34 which is lost through the side walls of the sensing fiber 40 (because it is refracted beyond the sensing fiber 40's acceptance angle for wave guiding the excitation light 34).

In general, a typical GRIN lens 36 may emit the excitation light 34 with an output half-angle of about 5° to 10°. Since most glass optical fibers may accept the excitation light 34 through a half-angle of about 12° to 25°, and since plastic fibers may accept the excitation light 34 at half-angles up to about 30°, or more, considerable variation in the cone half-angle of the excitation fiber 40's tip 38 may be allowable.

For example, if the cone half-angle of the excitation fiber 40's tip 38 was 35°, a point on the face of the conical tip 38 may receive the excitation light 34 from the lens 36 over a ±8° solid angle. Thus, the excitation light 34 exiting from the excitation fiber 40 would preferentially exit the excitation fiber 40 over an angular range of approximately 10° to 25°.

Alternatively, the excitation fiber 40's end 38 may not form a true cone, but may have a more complex optical shape which helps to compensate for the various angles at which the excitation light 34 may enter the excitation fiber 40's end 38.

It is understood that although the excitation fiber's end 38 is illustrated in FIG. 3 as having a convex, or protruding, cone shape, the end 38 may instead have a concave cone shaped pit of the same size and shape. Such a conical pit may be formed in any suitable way. For example, starting with an excitation fiber 40 having a flat end 38, the excitation fiber's end 38 may first be heated to the point where it is soft enough to take an impression from a previously prepared convex conical tool, which may then be pressed against the end 38 until the desired conical pit has been formed. Alternatively, such a conical pit may be formed by machining, either with mechanical tools or with a laser.

Although the excitation fiber's end 38 may preferably be a substantially complete cone (either convex or concave), whose side walls make a uniform angle with respect to the longitudinal axis of the excitation fiber 40, it is understood that the end 38 may also be only a portion of a full cone (either convex or concave), and its side walls may not make a perfectly uniform angle with respect to the excitation fiber 40's longitudinal axis.

Alternatively, instead of the excitation fiber 40's end 38 having a convex or concave cone shape, other optical arrangements may be used to favorably redirect the excitation light rays 34 entering the excitation fiber 40's end 38. Such optical arrangements may include the use of spherical micro-lenses or other rotationally symmetric convex or concave shapes formed as part of the fiber 40's end 38, or formed as separate elements mounted onto or adjacent to the end 38.

Figure 4:
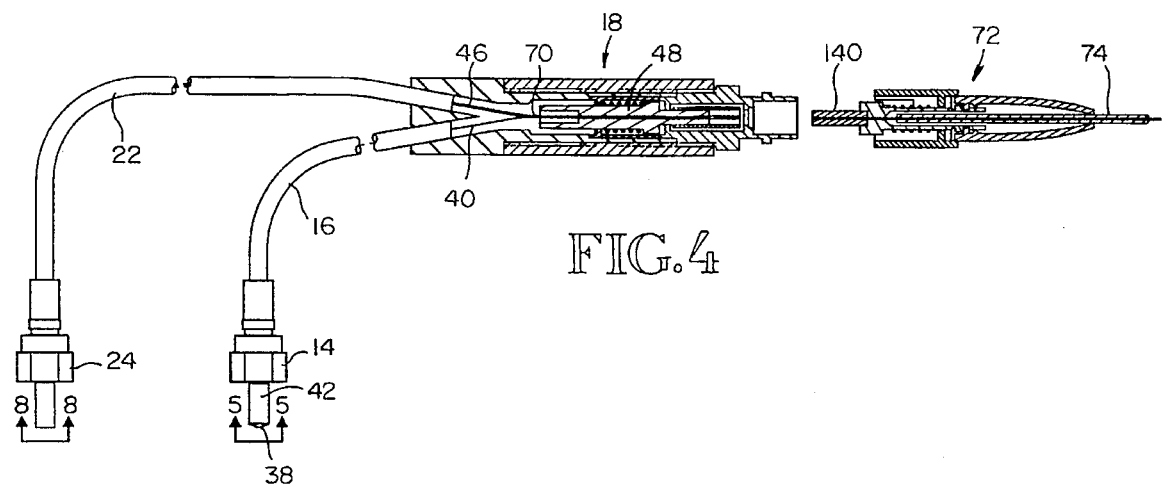
FIG. 4 is an elevational view, partly in longitudinal cross-section, of a portion of the present invention showing the excitation optical fiber cable, the sensor interface connector, the sensor connector, and the return light optical fiber array cable.

As seen in FIG. 4, the other end of the excitation cable 16 may terminate in a sensor interface connector 18. Also terminating in the sensor interface connector 18 may be one end of the return light optical cable 22; which may be of any suitable conventional construction, and which may comprise an array of at least several return light optical fibers 46.

Such an array of return light fibers 46 may not extend the entire length of the return light optical cable 22. For example, as best seen in FIG. 4B, the interface connector 18 may further comprise a tube 19 within which the return light fibers 46 may be optically spliced directly to the light receiver module 26's receiver optical fiber 94 (see also FIG. 15), by being butted up against, and adhesively joined to, the receiver optical fiber 94. The receiver optical fiber 94 may be selected to have an end area sufficient to at least generally encompass the combined end areas of the individual return light fibers 46. Such receiver optical fiber 94 may extend from the splice in the interface connector 18 to the receiver module 26.

Referring now to FIGS. 4, 4A, 6, 8, and 9–9A, an optical fiber bundle 70 may be fashioned within the interface connector 18 from the excitation cable 16's excitation fiber 40, and from the return light cable 22's array of return light fibers 46. The excitation fiber 40 may form the center element of the bundle 70, and the array of return light fibers 46 may be symmetrically arrayed about the excitation fiber 40, as seen. The size of the end of excitation fiber 40 in connector 18 may be up to about 80% of the size of the end of sensor fiber 76 in connector 18.

By way of example, in the FIGS. 6, 8, 9 and 9A embodiment, the fiber bundle 70 may comprise one excitation fiber 40 and six return light fibers 46, each about 250 microns in diameter. The sensor optical fiber 76 may be about 600 microns in diameter.

With reference to the FIGS. 10 and 10A embodiment, the optical fiber bundle 70a may comprise one excitation fiber 40a, about 250 microns in diameter, and four return light fibers 46a, each about 500 microns in diameter. The sensor optical fiber 76a may be about 800 microns in diameter.

In the FIGS. 11 and 11A embodiment, the fiber bundle 70b may comprise one excitation fiber 40b, about 250 microns in diameter, and four return light fibers 46b, each about 750 microns in diameter. The sensor optical fiber 76b may be about 1,200 microns in diameter.

The theory, structure and operation of the fiber bundles 70a, 70b, the excitation fibers 40a, 40b, the return light fibers 46a, 46b, and the sensor fibers 76a, 76b of FIGS. 10–11A may be the same as, or similar to, the theory, structure and operation of the fiber bundle 70, the excitation fiber 40, the return light fiber 46, and the sensor fiber 76 of FIGS. 6, 8 and 9–9A, except for those express or implied differences which may be apparent from all of the disclosures herein.

It is understood that there may be more than one excitation fiber 40; each excitation fiber 40 may have a diameter which is larger, or smaller, than in the examples set forth above; all of the excitation fibers 40 may not have the same diameter; and all of the excitation fibers 40 may not be of the same material.

It is also understood that there may be fewer, or more, return light fibers 46 than in the examples set forth above; the return light fibers 46 may be larger, or smaller in diameter than in the examples set forth above; all of the return light fibers 46 may not be of the same material, or of the same diameter; and all of the return light fibers 46 may not be symmetrically arranged around the excitation fiber 40.

It is further understood that there may be more than one sensor fiber 76; each sensor fiber 76 may have a diameter which is larger, or smaller, than in the examples set forth above; all of the sensor fibers 76 may not have the same diameter; and all of the sensor fibers 76 may not be of the same material.

The sensor interface connector 18 may be any suitable connector such as, for example, a conventional ST-style optical fiber connector. Such a conventional ST-style connector may be modified so that its connector pin 48 may contain a precision drilled bore 49 on its longitudinal axis, which may be sized to closely fit the optical fiber bundle 70.

The excitation and return fibers 40, 46 may be held in place in the bore 49 in any suitable way, such as by the use of a conventional optical fiber epoxy. In order to help prevent undesirable transfer of the excitation light 34 from the excitation fiber 40 to the return fibers 46, the optical fiber epoxy may be loaded with a suitable amount of an opacifier which is very absorptive in the excitation light 34's wave band.

For example, if the excitation light 34 has a wavelength of about 635 nm, as was described above, a suitable epoxy/opacifier mixture may preferably contain about 0.5% carbon black; or about 0.5% of a blue dye called Acetosol Blue GLS, manufactured by Sandoz Colors and Chemicals of Hanover, N.J., which is very absorptive in the 600 to 700 nm wave band, and which dissolves easily in the optical fiber epoxy.

Epoxy or suitable epoxy/opacifier mixtures may also be used to hold the excitation fiber 40 in the connector pin 42 of the transmitter connector 14; to hold the sensor fiber 76 in the sensor connector 72; and to hold the return light fibers 46 in the receiver connector 24. In such cases where an opacifier is used, the opacifier may be selected to prevent any undesired external light from reaching the fibers 40, 46, 76.

The sensor 20 may be connected to the interface connector 18 by an optical fiber sensor connector 72 and by an optical fiber sensor cable 74, both of which carry the sensor fiber 76. The sensor fiber 76 may carry the excitation light 34 from the excitation fiber 40 to the sensor 20, and may carry the sensor modulated return light 47 from the sensor 20 to the array of return light fibers 46. The distal end of the sensor fiber 76 may form the sensor 20's sensing fiber; or, if it does not, it may be optically coupled to the sensor 20's sensing fiber in any suitable way.

The sensor cable 74 may be of any suitable conventional construction. The sensor connector 72 may be any suitable conventional optical fiber connector, such as a conventional ST connector. For simplicity and clarity, the mechanical details and operation of the ST connector 72 illustrated in FIGS. 4 and 4A will not be described, since they are all conventional and well known in the art.

Figure 4A:
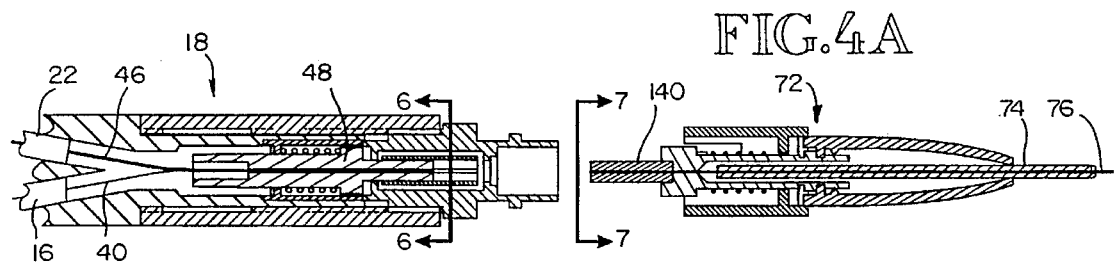
FIG. 4A is an enlarged view of the sensor interface connector and the sensor connector illustrated in FIG. 4.
Figure 4B:
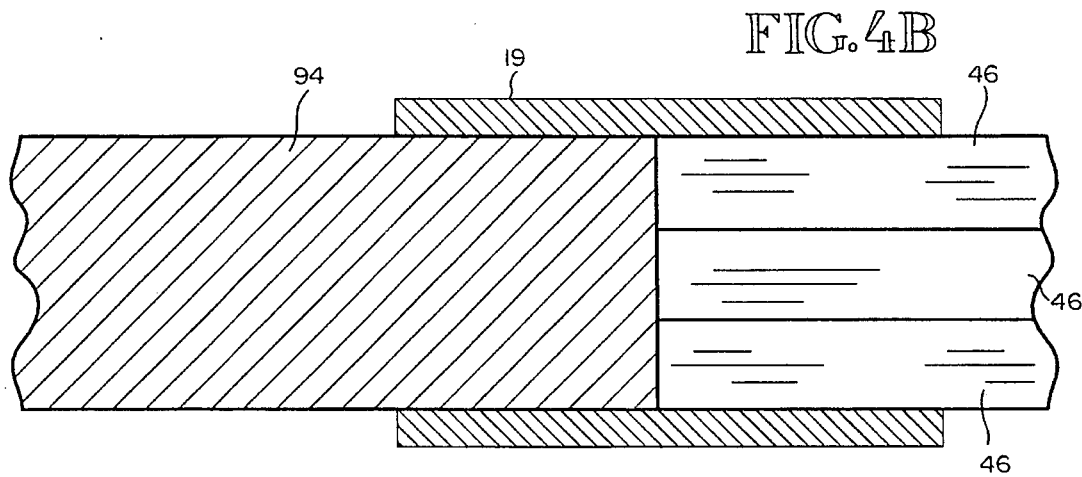
FIG. 4B is an enlarged view of an alternative embodiment of a portion of the sensor interface connector illustrated in FIG. 4, partly in longitudinal cross-section, and partly elevational.
Figure 5:
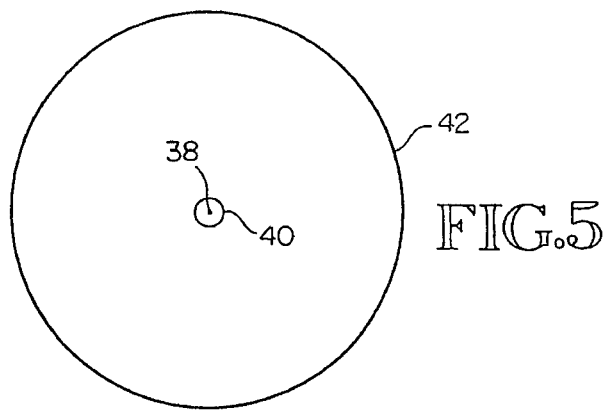
FIG. 5 is an end view of the connector pin in the transmitter connector, taken along line 5—5 of FIG. 4.

The conventional ST connectors 18, 72 illustrated in FIGS. 4, 4A appear different from each due to the fact that many different manufacturers make ST-type connectors, and their ST connectors may not all be exactly the same in the details of their fabrication and construction.

Important functions of the interface connector 18 and sensor connector 72 may include coaxially aligning and axially loading the fiber bundle 70 and the sensor fiber 76 with respect to each other. These functions may be important because maintaining intimate contact between the fiber bundle 70 and the sensor fiber 76 may be needed for maximum transfer of the excitation light 34 from the fiber bundle 70's excitation fiber 40 to the sensor fiber 76; and for maximum transfer of the sensor modulated return light 47 from the sensor fiber 76 to the fiber bundle 70's array of return light fibers 46.

However, an important aspect of the present invention may be that even if there happens to be a considerable error in the lateral alignment between the fiber bundle 70 and the sensor fiber 76, it may still be highly probable that the excitation light 34 from the fiber bundle 70's excitation fiber 40 will be delivered to the sensor fiber 76.

Such unexpected toleration of lateral misalignment between the fiber bundle 70's excitation fiber 40 and the sensor fiber 76 may be due to the fact that the excitation fiber 40 may preferably have a diameter which may be substantially less than that of the sensor fiber 76. This may create a situation where the end face of the sensor fiber 76 not only completely overlaps the end face of the excitation fiber 40, but also extends some distance outwardly past the end face of the excitation fiber 40. This is best seen in FIGS. 9–11A.

For example, it will be recalled that in the embodiment shown in FIGS. 11 and 11A, the diameters of the excitation and sensor optical fibers 40b, 76b may be 250 microns and 1,200 microns, respectively. It then follows that if the excitation and sensor fibers 40b, 76b are coaxially aligned, the end face of the sensor fiber 76b will completely overlap the end face of the excitation fiber 40b; and will, in addition, extend outwardly past the end face of the excitation fiber 40b by 475 microns on all sides of the end face of the excitation fiber 40b.

Thus, the excitation and sensor fibers 40b, 76b would have to laterally misaligned by at least 475 microns before any part of the end face of the excitation fiber 40b was no longer overlapped by the end face of the sensor fiber 76b; and would have to be laterally misaligned by at least 725 microns before no part of the end face of the excitation fiber 40b was overlapped by the end face of the sensor fiber 76b.

Similarly, another important aspect of the present invention may be that even if there happens to be a considerable error in the lateral alignment between the fiber bundle 70 and the sensor fiber 76, most of the sensor modulated return light 47 from the sensor 20 may still likely be delivered from the sensor fiber 76 to the fiber bundle 70's array of return fibers 46.

Such unexpected toleration of lateral misalignment between the fiber bundle 70's array of return fibers 46 and the sensor fiber 76 may be due to the fact that the diameter of the sensor fiber 76 may be substantially less than the cumulative total diameter of the fiber bundle 70. As best seen in FIGS. 9–11A, this may create a situation where the end face of the sensor fiber 76 may be substantially overlapped by the end faces of the fiber bundle 70's array of return fibers 46.

For example, it will be recalled that in the embodiment shown in FIGS. 11 and 11A, the diameter of the excitation fiber 40b may be 250 microns, the diameters of the return fibers 46b may be 750 microns, and the diameter of the sensor fiber 76b may be 1,200 microns. It then follows that, as best seen in FIG. 11A, if the excitation and sensor fibers 40b, 76b are coaxially aligned, the end faces of the fiber bundle 70's array of return fibers 46b may nearly completely overlap the end face of the sensor fiber 76b; and may, in addition, periodically extend outwardly past the end face of the sensor fiber 76b for a distance of up to about 305 microns.

Thus, the fiber bundle 70's array of return light fibers 46b and the sensor fiber 76b would have to laterally misaligned by at least about 445 microns before the end face of at least one of the return fibers 46b was no longer overlapped by the sensor fiber 76b.

With a sensor fiber 76 of any particular given size, such desirable overlap and outward extension of the end faces of the fiber bundle 70's array of return fibers 46 with respect to the end face of the sensor fiber 76 may be accomplished in one or more of the following ways, either alone or in combination with each other.

First, such desirable overlap and outward extension may be provided by suitably selecting how many excitation, return and sensor fibers 40, 46, 76 are utilized.

Second, such desirable overlap and outward extension may be accomplished by adding to the fiber bundle 70 one or more suitably sized filler return light fibers 46, to fill in the spaces between the fiber bundle 70's array of return light fibers 46 and the excitation fiber 40.

Third, such desirable overlap and outward extension may be provided by adding to the fiber bundle 70 one or more additional whole or partial rings of return fibers 46 on top of the next lower ring of return fibers 46.

Fourth, such desirable overlap and outward extension may be accomplished by eliminating the excitation fiber 40 and the array of return fibers 46 as discrete fibers, and replacing them all with a single, two layer optical fiber having concentric light conducting areas. In such a two layer optical fiber, the inner layer, or center, of the optical fiber may be selected to act as a replacement for the discrete excitation fiber 40; while the annular outer layer of such a two-layer optical fiber may be selected to act as a replacement for the array of discrete return fibers 46.

Fifth, such desirable overlap and outward extension may be accomplished by suitably selecting the diameters of the excitation, return and sensor fibers 40, 46, 76, with respect to each other.

In this regard, it should be noted that, in general, the optical fibers 40, 46 may comprise a light transporting core area, and a cladding around the core area which serves to help keep the transported light within the core area. For example, for a glass fiber 40, 46 having a nominal overall diameter of about 250 microns, its core may be about 200 microns in diameter, and its cladding may be about 25 microns thick. Similarly, a plastic fiber 40, 46 having a nominal overall diameter of about 250 microns may have a core diameter of about 230 microns and a cladding about 10 microns thick.

Thus, for a sensor fiber 76 of any given size, it may be useful to either remove the cladding entirely from the ends of the excitation and/or return fibers 40, 46 in the interface connector 18 (as by the use of a suitable chemical agent); or to use fibers 40, 46 having as thin a cladding as possible, in order to maximize the amount of overlap between the ends of the light transmitting cores of the fibers 40, 46 with end of the light transmitting core of the sensor fiber 70.

Regarding the three embodiments illustrated FIGS. 6, 8 and 9–11A, it has been discovered that if their excitation fibers 40, 40a, 40b and their sensor fibers 76, 76a 76b are coaxially aligned, then their arrays of the return fibers 46, 46a, 46b, may capture about 74%, 77%, and 86%, respectively, of the sensor modulated return light 47 which is returned from the sensor 20 through their respective sensor fibers 76, 76a, 76b.

Figure 12:
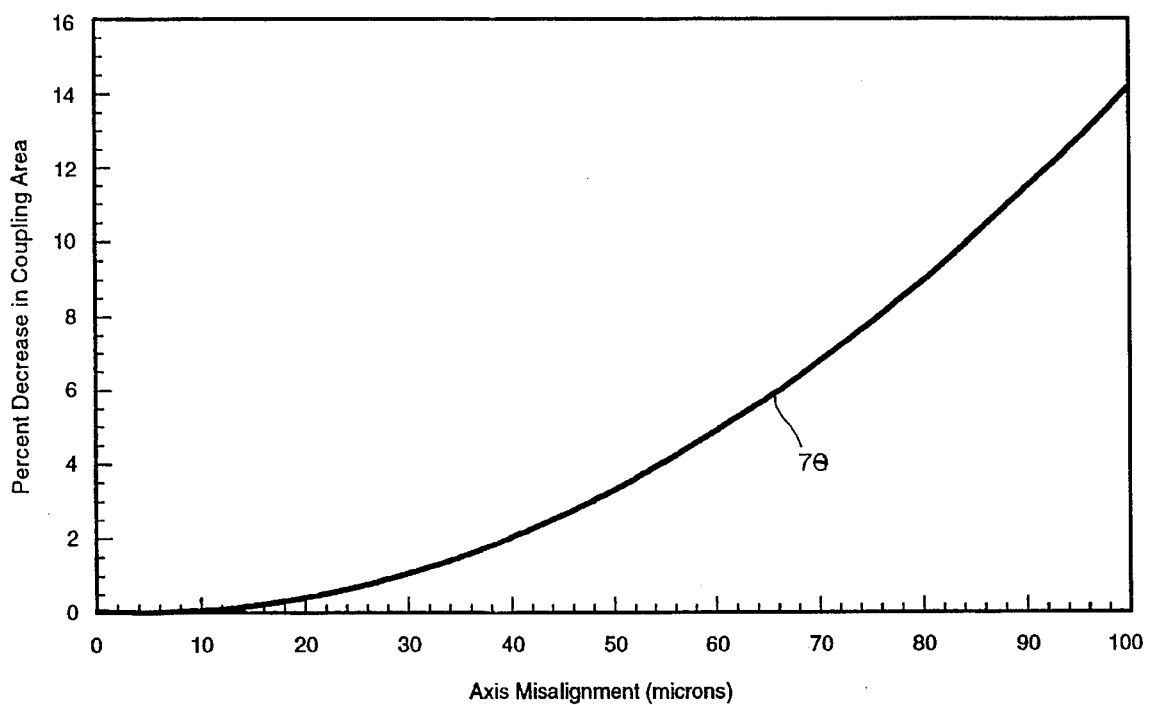
FIG. 12 is a graph showing the effect of misalignment between the sensor optical fiber and the array of return light fibers.

Turning now to the graph of FIG. 12, its curve 78 is for the FIG. 6, 8 and 9–9A embodiment. Similar curves 78 may apply to the FIGS. 10–10A and FIGS. 11–11A embodiments.

FIG. 12 vividly illustrates that even major lateral displacements between the fiber bundle 70's array of return light fibers 46 and the sensor fiber 76 may result in remarkably small changes in the overlap area between the return light fibers and the sensor fiber 76.

For example, as seen in FIG. 12, even if such lateral misalignment is as large as about 80 microns (i.e., about 32% of the diameter of one of the return fibers 46), then the overlap area between the fiber bundle 70's array of return fibers 46 and the sensor fiber 76 may decrease by only about 10 %.

This may be very important since the amount of the sensor modulated return light 47 from the sensor 20 which may be successfully coupled from the sensor fiber 76 to the fiber bundle 70's array of return fibers 46, may be a direct function of the overlap area between the sensor fiber 76 and the array return fibers 46. Similar comments may apply to the FIGS. 10–10A and 11–11A embodiments.

As a practical matter, in the present state of the art it is very easy to achieve alignments to within about 25 microns by using standard precision machining practices. With alignments of this accuracy, the excitation, return and sensor fibers 40, 46, 76 in the FIGS. 6, 8, and 9–9A embodiment may have diameters which are up to about 50% smaller than the diameters which were set forth above by way of example; thereby permitting use of high quality, plentiful and inexpensive standard telecommunications fibers which are only 125 microns in diameter for the excitation and return fibers 40, 46, and which are only 300 microns in diameter for the sensor fiber 76. Similar comments may apply to the FIGS. 10–10A and 11–11A embodiments.

It has been discovered that the fiber bundle 70's annular array of return fibers 46 may be remarkably efficient at collecting the sensor modulated return light 47 from the sensor fiber 76, if the sensor 20 is of the evanescent wave excited, fluorescence light-generating type of intrinsic sensor 20 which was mentioned above. It will be recalled that such evanescent wave excited, fluorescence light-generating intrinsic sensors 20 may depend on modulation of the excitation light 34 in a longitudinally extended, thin, annular layer of fluorophore(s) on the outer surface of the sensor 20's sensing fiber, to produce the sensor modulated return light 47.

It has been discovered that when such modulation of the excitation light 34 is modeled, by using light ray tracing techniques, for a sensor 20 having a large, multimode, sensing fiber capable of propagating light by several thousand different modes, the majority of the sensor modulated return light 47 may be concentrated in a small annular zone near the surface of the sensor 20's sensor fiber 76. Most optical fibers having a diameter larger than about 100 microns are capable of propagating light by several thousand different modes.

Figure 13:
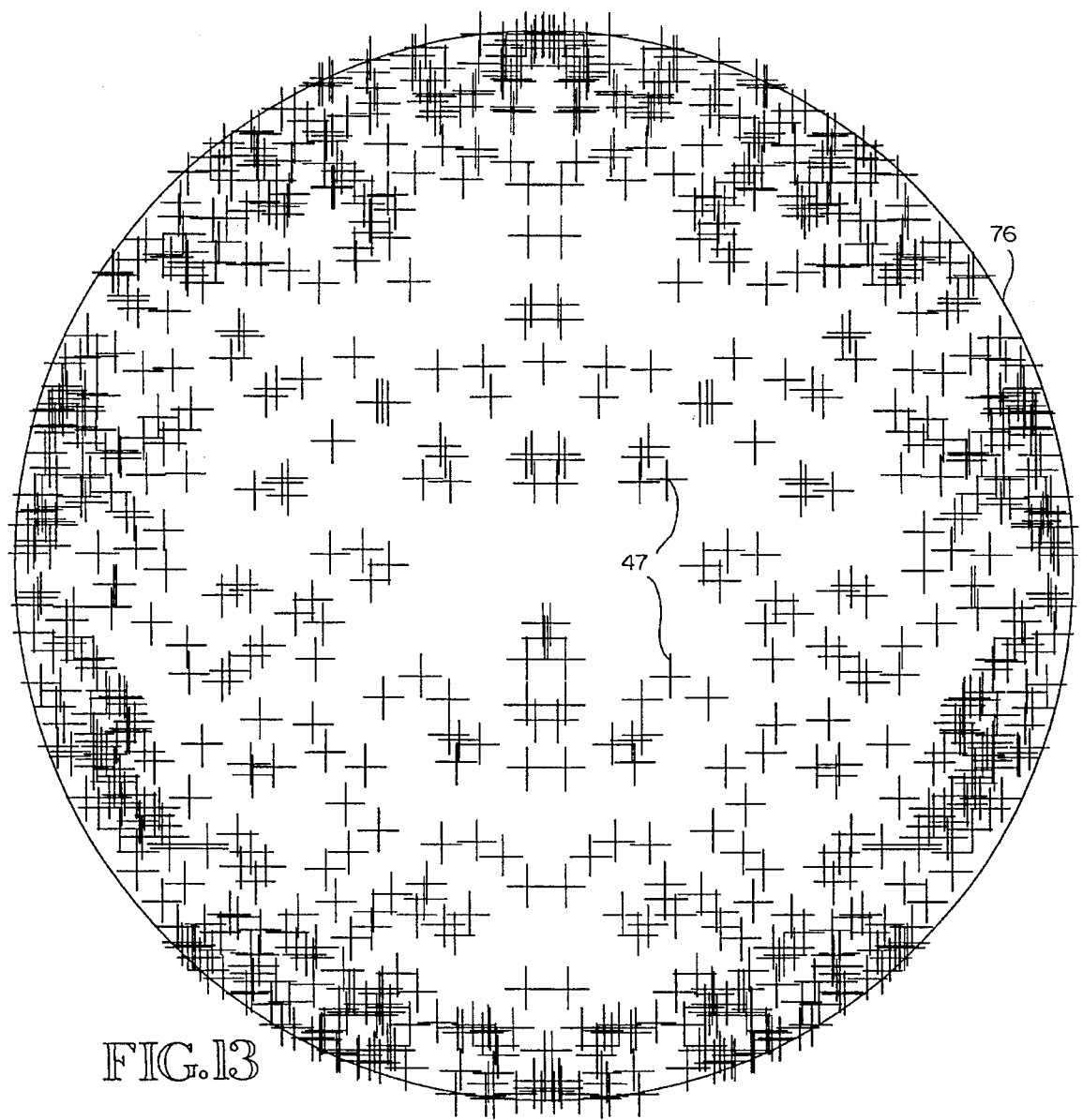
FIG. 13 is a light ray intercept diagram, taken at the end of the sensor optical fiber which is located in the sensor connector, showing the distribution of the returning light rays from the optical sensor across the end of the sensor optical fiber.
Figure 14:
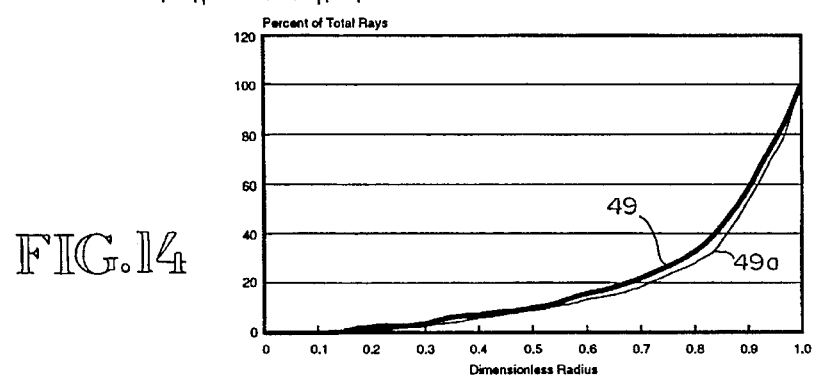
FIG. 14 is a graph showing the percentage of such returning light rays as a function of the dimensionless radius of the sensor optical fiber.

Such a small annular zone in the sensor fiber 76 which carries the majority of the sensor modulated return light 47 is exemplified in FIGS. 13 and 14 for the 600 micron diameter sensor fiber 76 of the FIGS. 6, 8 and 9–9A embodiment.

FIG. 13 is a light ray intercept diagram for the end of the sensor fiber 76 which is located adjacent to the fiber bundle 70. Each cross 47 in FIG. 13 depicts one ray of the sensor 20's modulated return light 47.

The curves 49, 49a in FIG. 14 depict the percentage of the total light rays of the sensor modulated return light 47, in the sensor fiber 76, as a function of the dimensionless radius of the sensor fiber 76. The curve 49 is for a sensor 20 having a sensing fiber with cylindrical walls; while the curve 49a is for a sensor 20 having a tapered sensing fiber.

As seen in FIGS. 13 and 14, about 70% of the sensor modulated return light 47 may be concentrated in an annular zone extending over the outer 20% of the sensor fiber 76's cross-section.

Thus, it has been discovered that the fiber bundle 70's annular array of return fibers 46 may be remarkably effective at collecting the sensor modulated return light 47 from the sensor fiber 76. This is because, as is best seen in FIG. 9A, the alignment of the fiber bundle 70's return fibers 46 with the sensor fiber 76 may emphasize maximum overlap of the end faces of the return fibers 46 with the energy dense, outer 20% of the corresponding end face of the sensor fiber 76. The annular array formed by the input ends of return fibers 46 may be at least about 20% wider than the annular zone of sensor fiber 76.

At the same time, it has been further discovered that there may be very little penalty to be paid by intentionally injecting the excitation light 34 from the excitation fiber 40 into the central region of the sensor fiber 76. This may be because, as is seen in FIG. 13, there may be very little sensor modulated return light 47 in the central region of the sensor fiber 76, and so failing to recover it with the fiber bundle 70's return fibers 46 may result in a negligible loss of the sensor modulated return light 47.

Similar light ray intercept diagrams, and comments, would apply to the FIGS. 10–10A and 11–11A embodiments.

It has been further discovered that the use of a fiber bundle 70 having an excitation fiber 40 which is separate from the return fibers 46 allows the fibers 40, 46 to be selected for properties and used in an entirely different, and favorable, manner as compared to a single, bidirectional fiber which is used in most conventional optical fiber sensor systems to both convey the excitation light 34 to the sensor, and to convey the sensor modulated return light 47 away from the sensor.

All of the forgoing may be particularly true if the sensor 20 was an evanescent wave excited, fluorescence light-generating type of intrinsic sensor 20, and if such a single, bidirectional fiber extended from the sensor 20 to the transmitter 12 and receiver 26, and served both to both transport excitation light 34 from the transmitter 12 to the sensor 20, and to transport sensor modulated return light 47 from the sensor 20. In such a case the excitation light 34 may be injected into the single, bidirectional fiber, and the sensor modulated return light 47 may be recovered from the single, bidirectional fiber through some suitable combination of spectral filters and mirrors. However, certain compromises may have to be made in order to provide good bidirectional optical communication through such a single, bidirectional fiber.

These compromises will be outlined by first describing the optical fiber attributes of a good optical fiber bundle 70 having separate excitation and return fibers 40, 46; and then showing the difficulty of providing this level of performance with a system having a single, bidirectional fiber.

For example, it may be preferable, in general, that the excitation fiber 40 be low in loss and high in acceptance angle, or NA, where NA is defined as:

$$NA = \sin(\theta), \quad \text{Equation 1}$$

and where θ is the largest angle relative to the longitudinal axis of the excitation fiber 40 that the excitation light 34 can be injected into the excitation fiber 40 in air or vacuum, and still be transported by the excitation fiber 40.

Most glass-on-glass telecommunications fibers may have relatively low NAs, in the range of about 0.10 to 0.22; while specialty glass fibers having plastic cladding may have NAs (for short lengths), of up to about 0.42. On the other hand, low melting point glasses used in imaging conduits, and plastic optical fibers may have relatively high NAs, ranging from about 0.4 to 0.90.

For present purposes, "low NA" fibers may be defined to be those with NAs less than about 0.3; "intermediate NA" fibers may be defined as those with NAs from about 0.3 to about 0.4; and "high NA" fibers may be defined to be those with NAs of about 0.4, or more.

A high NA may be desirable since it may maximize the amount of excitation light 34 from the light source 28 which may be successfully injected into the excitation fiber 40, and thus delivered to the sensor 20. When the amount of excitation light 34 to the sensor 20 is maximized, the amount of sensor modulated return light 47 from the sensor 20 may also be maximized.

This may enable the sensor 20 to be more sensitive, and to successfully detect levels of the target chemical which may be much lower than might otherwise be the case. When the excitation fiber 40 has a high NA, the NAs of the sensor fiber 76 and the sensor 20's intrinsic sensing fiber may also have to be of a similarly high value, for maximum transfer of excitation light 34 between them.

A high NA for the fiber bundle 70's array of return light fibers 46 may also be desirable, in order to maximize the amount of the sensor modulated return light 47 which may be delivered by the array of return light fibers 46 to the light receiver module 26. When the array of return light fibers 46 has a high NA, the NAs of the sensor fiber 76 and the sensor 20's intrinsic sensing fiber may also be high, in order to allow efficient coupling and maximum transfer of the sensor modulated return light 47 between them.

For example, for an evanescent wave excited, fluorescence light-generating type of sensor 20, optimum recovery of the sensor modulated return light 47 may require the return light optical system (i.e., the sensor 20's sensing fiber, the sensor fiber 76, and the return fibers 46), to all have similarly high NAs.

If such a sensor 20's sensing fiber is quartz and immersed in water, the sensing fiber's NA may be, for example, about 0.58. As a general rule, the signal power of the return light 47 delivered to the receiver module 26 will be proportional to the square of the smallest NA in the return light optical system. Hence, a return light optical system having an optical fiber with an NA of 0.22 may transfer only about 14% of the return light 47's signal power that a sensor 20 having an intrinsic NA of 0.58 generates.

It may also be desirable that the excitation fiber 40, the sensor fiber 76, and the fiber bundle 70's array of return fibers 46 do not exhibit a phenomenon called "mode-shifting". "Mode shifting" for any optical fiber is where light launched into the fiber's input end under specific angular conditions (with respect to the fiber's longitudinal axis), comes out of the fiber's output end with a power profile having a different angular dependence.

Avoiding such "mode shifting" may be particularly important if the excitation light 34 is being injected into the input end of the excitation fiber 40 under carefully regulated conditions with respect to the fiber 40's longitudinal axis, in order to maximize excitation of the intrinsic sensor 20. In general, such "mode shifting" may be reduced by using high quality, relatively low NA, glass-on-glass fibers as the excitation, return and sensor fibers 40, 46, 76; or by making any particular fiber 40, 46, 76 so short that it may not have much effect in terms of "mode shifting".

In summary, the functions of the excitation fiber 40 and the return fibers 46 may be served best if they are high NA optical fibers. Although high NA fibers may work very well for recovery of the sensor modulated return light 47 in the present invention, they suffer from several drawbacks that may severely limit their use as the optical fiber in a system that utilizes a single, bidirectional optical fiber.

One drawback is that such high NA fibers may typically be made from high refractive index plastics or glasses that may not be optically perfect, in that they may have striae and other flaws that may undesirably refract and reflect the light which they are transporting, leading to undesirable mode shifting in a system using a single, bidirectional fiber. This drawback may be of concern with the present invention as well, but while this effect may be tolerated or designed around for the present invention, these internal imperfections also result in a large amount of the excitation light 34 being reflected or refracted back into such a single, bidirectional fiber, thereby undesirably flooding the light receiver module 26 with excitation light 34.

Such flooding of the light receiver module 26 with excitation light 34 may potentially overwhelm the ability of any optical filters in the receiver module 26, such as the dichroic filter 116 (See FIG. 15), to reject the excitation light 34, since no filter is perfect. As a result, any excitation light 34 which passes the optical filters in the receiver module 26 may be falsely detected as the sensor modulated return light 47. This may be very important since, as has been mentioned, the power level of the sensor modulated return light 47 may be very small, and any additional excitation light 34 falsely detected as sensor modulated return light 47 may give rise to significant measurement errors.

Such saturation of the light receiver module 26 with excitation light 34 may not be a problem in the present invention, since the high intensity excitation light 34 is carried in the excitation fiber 40, and any back-reflected excitation flare light 34 merely impinges harmlessly on the light source 28 in the light transmitter module 12. Also, the "mode shifting" described above may be of little consequence in the present invention's return fibers 46, since they are not being used to carry any of the excitation light 34 to the sensor 20.

A further potential drawback of using a high NA fiber in a system having a single, bidirectional fiber is that this type of fiber may intrinsically generate high levels of fluorescence when excited by the excitation light 34. The high levels of fluorescence may overwhelm the sensor modulated return light 47 generated by the sensor 20, particularly where the power level of the sensor modulated return light 47 is extremely low.

Another potential drawback of using a high NA fiber in a system having a single, bidirectional fiber, is that this type of fiber may exhibit a phenomenon called "Raman scattering" wherein molecules within the fiber may be vibrated at infrared frequencies if the excitation light 34 is of a short wavelength. This may result in the generation of beat frequency spectra that mimic the wave band of the sensor modulated return light 47, and thus may be very difficult to distinguish from the true sensor modulated return light 47. This may be a significant problem when the power level of the true return light 47 is extremely low.

Once again, the fiber bundle 70 approach of the present invention may not be afflicted with the above problems of fiber fluorescence and Raman scattering for at least two reasons. First, the return light fibers 46 only see low level sensor modulated return light 47, and thus do not, themselves, generate any significant amounts of fiber fluorescence or Raman scattering. Second, any fiber fluorescence and Raman scattering generated by the high level excitation light 34 in the excitation fiber 40 may never reach the return fibers 46. This is because any such excitation fiber 40 generated fiber fluorescence and Raman scattering may either be back-scattered into, and harmlessly lost, within the light source 28; or may be attenuated to a very low level by an optical absorber placed at the distal end of the sensor 20's sensing fiber.

If one turns to a comparatively low NA optical fiber such as a very high purity quartz-based fiber, in a system having a single bidirectional fiber in an effort to avoid the above drawbacks of high NA optical fibers, then one is faced with the problem that the amount of light which such low NA fibers may carry may be much less than that which higher NA fibers may carry, resulting in the multifunctional sensor system 10 possibly being less sensitive than might otherwise be the case.

It has been discovered that a low NA fiber may be used as the excitation fiber 40 in the present invention to control the above problem, with relatively little loss in the sensitivity of the multifunctional sensor system 10, if the excitation light 34 is transferred to the sensor 20 at a low NA and the sensor 20 incorporates means to adjust the excitation light's NA as necessary for optimal excitation of the sensor 20.

Since such a low NA excitation fiber 40 may be combined with high NA return fibers 46 for recovery of the sensor modulated return light 47, both the excitation and return fibers 40, 46 may be optimized separately to maximize the performance of the multifunctional sensor system 10 of the present invention.

A corollary advantage with the multifunctional sensor system 10 of the present invention, in contrast to a system having a single, bidirectional fiber, may be that the sensor 20 may be placed much further away from the transmitter module 12 and the receiver module 26, than might otherwise be the case. This may be because the receiver module 26 may detect much lower levels of sensor modulated return light 47, due to the fact that there may be much less light from non-sensor 20 sources reaching the receiver module 26 that could interfere with the detection of low level return light 47.

When used for the excitation fiber 40, high NA fibers may allow superior coupling of the excitation light 34 to the sensor 20. Light sources 28 such as LEDs emit light over a very wide angle, and a high NA fiber may maximize the capture and delivery of the excitation light 34 by the excitation fiber 40 from light sources 28 based on such wide-angle emitters.

Again, significant amounts of neither the excitation light 34 scattered within the excitation fiber 40, nor the fluorescence light generated with the excitation fiber 40, may reach the separate return fibers 46 because the fibers 40, 46 are not optically coupled directly together; because all backscattered light within the excitation fiber 40, regardless of wavelength, is returned harmlessly to the light source 28; and because left over excitation light 34 and forward scattered fluorescence light generated by the excitation fiber 40 may be absorbed by a light absorbing trap at the distal end of the sensor 20's sensing fiber.

Since the separate return fibers 46 may not be subjected to high levels of excitation light 34, or to luminescence light generated by the excitation fiber 40, virtually all of the light they receive may be sensor modulated return light 47, which, as has been mentioned, may be of a very low power level. Thus, the fibers selected for use as the return fibers 46 may be selected with little concern as to their internal scattering or fluorescing characteristics. This may allow much higher NA fibers to be used for the return fibers 46 than might otherwise be the case, which may typically result in substantial increases in the amount of sensor modulated return light 47 being successfully transported by the return fibers 46 to the receiver module 26.

It has been discovered that using high NA plastic return fibers 46 may have several other advantages. First, as was explained above, such high NA return fibers 46 may have an inherently higher capacity for capturing sensor modulated return light 47 that makes large angles with respect to the longitudinal axis of the sensor fiber 76. This may be very important and very desirable in the context of the present invention since, as was explained above with respect to FIGS. 13 and 14, such large angle return light 47 may constitute a disproportionately large fraction of the total return light 47 from a sensor 20 which is an evanescent wave excited, fluorescence light-generating type of intrinsic sensor. Thus, the use of such high NA plastic fibers for the array of return light fibers 46 may desirably maximize the amount of return light 47 which may reach the light receiver module 26 from an evanescent wave excited, fluorescence light-generating type of intrinsic sensor 20.

Second, high NA plastic return fibers 46 are much more flexible than glass return fibers 46 of the same diameter, typically exhibiting a stiffness that may be less than $\frac{1}{20}$th of that of a glass return fiber 46 of the same diameter. This may be important since, for any given desired flexibility for the return light cable 22, high NA plastic return fibers 46 may be used having a much larger diameter than would be the case if glass return fibers 46 were used. As an example, polymethmethacrylate (PMMA) plastic fibers of 1 mm diameter have a minimum bend radius that is less than 1.6 cm, whereas the minimum bend radius for a 1 mm quartz glass fiber would be more than 30 cm.

The use of large diameter return fibers 46 may be important since they may (as compared to smaller diameter return fibers 46), offer the advantages of capturing more of the sensor modulated return light 47, and permitting more misalignment between the sensor fiber 76 and the array of return light fibers 46. Thus, the use of flexible, high NA plastic return fibers 46 may permit these advantages to be secured without sacrificing any needed flexibility of the return light cable 22.

Third, plastic return fibers 46 may have the benefit of being, for any given desired amount of light guiding ability, much less costly than glass return fibers 46. As an example, a 1 mm diameter PMMA fiber with 0.48 NA will have about 250 times the light guiding cross-sectional area of a 0.0625 mm core telecommunications fiber with a 0.22 NA, yet may be comparable in cost.

Thus, an array of such large diameter, high NA plastic return light fibers 46 may convey an exceptionally large proportion of the total return light 47 from the sensor fiber 76 to the light receiver module 26, as compared to an array of small diameter, low NA return fibers 46.

Figure 15:
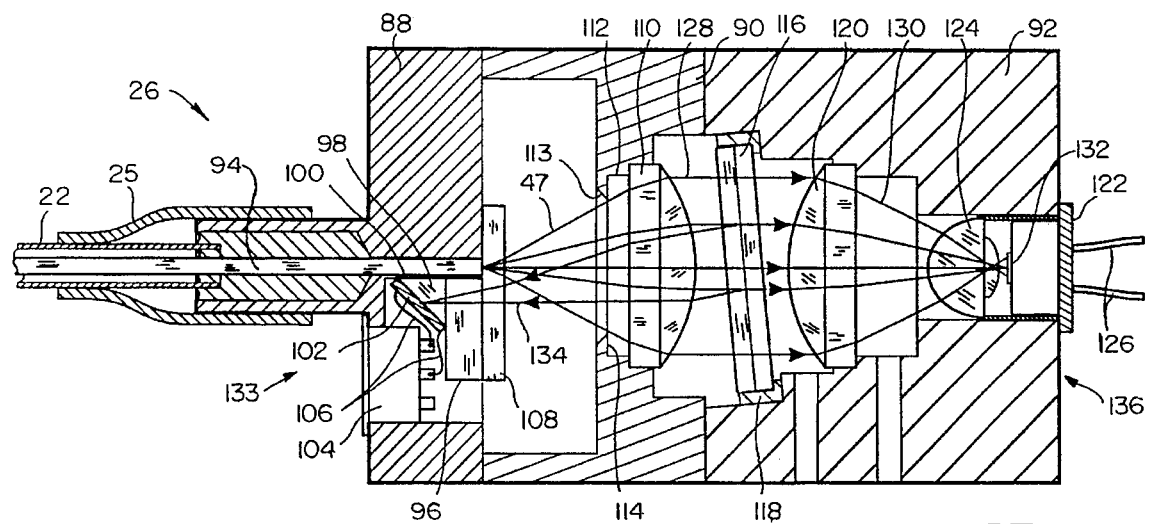
FIG. 15 is an enlarged, fragmentary elevational view, partly in cross-section, showing the return light optical fiber array cable; the receiver connector; and the light receiver module.

Turning now to FIGS. 1 and 15, the sensor modulated return light 47 may be conveyed to the receiver module 26 by the array of return light fibers 46 in the return light cable 22, which may terminate in a receiver connector 24 (not seen in FIG. 15), on the exterior of the receiver module 26. The receiver connector 24 may be any suitable conventional optical connector, such as an ST connector. For simplicity and clarity, the mechanical details and operation of the receiver connector 24 illustrated in FIGS. 1 and 4 will not be described, since they are generally conventional and well known in the art. The connector pin in the ST receiver connector 24 may be drilled out to accept the array of return fibers 46, which may then be potted in place with epoxy. An epoxy/opacifier potting mixture may not be needed for this purpose.

The primary functions of receiver connector 24 may be to hold the return fibers 46 and the receiver fiber 94 so that their longitudinal axes are parallel with respect to each other; and to provide an axial load to maintain an intimate contact between the end faces of the return fibers 46 and the end face of the receiver fiber 94.

Alternatively, as was discussed above, the return light 47 from the array of return fibers 46 may be transferred to the receiver fiber 94 within the sensor interface connector 18 (or at any other suitable location in the return light cable 22). In such a case, the receiver fiber 94, rather than the array of return fibers 46, would lie within the return light optical cable 22, and would convey the return light 47 to the receiver module 26.

In such an event, the return light optical cable 22 and the receiver fiber 94 may be potted in place in the receiver module 26, as seen in FIG. 15, and a flexible cover 25 may be provided.

The receiver module 26 may comprise left, center and right housings 88, 90 and 92, respectively. Within the left housing 88 may be located the single receiver optical fiber 94, whose end may have been polished flush with the interior face of the left housing 88 after the receiver fiber 94 was secured in the left housing 88. The return light 47 from the array of return fibers 46 may be transferred to the receiver fiber 94 within the receiver connector 24.

The receiver fiber 94 may have a diameter which is at least as large as the maximum combined diameter of the array of return fibers 46; although the receiver fiber's diameter may be the same as, or smaller than the maximum combined diameter of the array of return fibers 46. Although only one receiver fiber 94 is illustrated, there may be more than one receiver fiber 94; and if there is more than one receiver fiber 94, their diameters may not all be the same.

Also mounted within the left housing 88 may be a glass mounting block 96 incorporating a dichroic filter designed to pass excitation light only; a glass prism 98; a layer of light absorbing material 100; a bare photodiode chip 102; and an electrical connector 104, which may be electrically connected to the photodiode chip 102 with wires 106.

Mounted to the right side of the left housing 88 may be a filter 108 that excludes or attenuates extraneous light, such as sunlight, and passes only excitation light 34 and sensor modulated return light 47. The filter 108 may also serve to minimize the scattering effect of dust particles that might otherwise occlude part of the receiver fiber 94's right end face, and may serve as a mount for the subassembly comprising the mounting/filter block 96, the prism 98 and the photodiode chip 102.

The receiver module 26's center housing 90 may have a plano-convex lens 110 mounted to its right side, as seen in FIG. 15; and may have a pair of stepped openings 112, 114 for the passage of the return light 47. The lens 110 may be any suitable lens, and may be made from any suitable optical glass, such as LASFN18 manufactured by Schott Optical Glass Inc. of Duryea, Pa., which may have a refractive index of 1.91 in the wave band(s) of interest.

A lens 110 with an unusually high refractive index may be desirable to help collect as many of the rays of the sensor modulated return light 47 as possible. The stepped opening 112 may be provided with a sharp knife edge 113, as best seen in FIG. 15, to help exclude rays of the sensor modulated return light 47 which are outside of the opening 112, and to help minimize the generation and collection of uncontrolled stray light within the light receiver module 26.

The light receiver module 26's right housing 92 may include a primary optical-electrical circuit 136 comprising a dichroic filter 116 (installed with a holder 118); a plano-convex lens 120; a prepackaged sensor photodiode 122, including a photodiode die 132, and an optional integral lens 124; and a pair of electrical wires 126. The lens 120 may be the same as the lens 110.

During operation of the light receiver module 26, the sensor modulated return light 47 from the receiver fiber 94 may pass through the filter 108, be formed into a collimated beam 128 by the lens 110, and then impinge on the dichroic filter 116. The dichroic filter 116 may be selected to have a passband which encompasses the sensor wave band (i.e, the wave band of the sensor modulated return light 47); and to reflect at least some of the light of other wavelengths (such as light in the wave band of the excitation light 34). Although a dichroic filter 116 is illustrated, any other kind of suitable conventional filter 116 may be used.

The filtered sensor modulated return light 130 from the dichroic filter 116 (which contains information regarding the detected target chemical), may be focused by the lens 120 (and by any lens 124 in the packaged photodiode 122), onto the photodiode die 132 in the packaged photodiode 122, to generate a sensor electrical signal on photodiode wires 126 which contains information regarding the detected target chemical.

The lenses 120, 124 may be selected to focus the filtered sensor light 130 to a very small spot, to minimize the size of the photodiode die 132. This may be desirable since it may improve the noise rejection and signal response of the packaged photodiode 122 under high gain conditions, particularly when synchronous detection techniques are utilized. A synchronous detection technique is one in which the light source 28 is sequenced on and off, so that suitable electronics connected to the wires 126 may synchronously average the difference in the sensor electrical signal output between the on and off periods. Such electronics may be set up to subtract the sensor electrical signal present when the light source 28 is off i.e., when theoretically the sensor electrical signal should be zero.

Referring again to FIG. 15, the light receiver module 26 may include a secondary optical-electrical circuit 133 comprising the dichroic filter 116, the lens 110, the filter 108, the mounting/filter block 96, the prism 98, the layer of light absorbing material 100, the reference photodiode 102, the electrical wires 106, and the electrical connector 104.

As seen in FIG. 15, the dichroic filter 116 may be tilted at a small angle, such as about 5°, with respect to the longitudinal axis of the collimated beam 128. Reflected light 134 from the tilted dichroic filter 116 may pass through the lens 110 a second time, which may focus the reflected light 134 onto the reference photodiode 102. The reference photodiode 102 may be located just to one side of the longitudinal axis of the receiver optical fiber 94, and may be positioned such that all of the reflected light 134 from the lens 110 falls upon it, regardless of the focal point of any particular light ray in the reflected light 134.

It should be kept in mind that, as was mentioned above, the dichroic filter 116 may be selected to have a passband which encompasses the sensor wave band (i.e, the wave band of the sensor modulated return light 47); and to reflect at least some of the light of other wavelengths (such as light in the wave band of the excitation light 34). Accordingly, the reflected light 134 from the dichroic filter 116 may comprise essentially only excitation light 34, and no sensor modulated return light 47.

On its way from the lens 110 to the reference photodiode 102, the reflected light 134 may pass through the filter 108; the mounting/filter block 96, and the prism 98; before reaching the reference photodiode 102. The reference photodiode 102 may be cemented face up on the prism 98, as seen in FIG. 15.

The majority of the reflected light 134 may be absorbed by the reference photodiode 102, to generate a reference electrical signal which contains information regarding the reflected light 134. The reference electrical signal may be conducted from the reference photodiode 102 to the electrical connector 104 by the pair of wires 106.

Any of the reflected light 134 which may not be absorbed by the reference photodiode 102 may be specularly reflected from the reference photodiode 102's surface onto the layer of light absorbing material 100, which may then absorb it. This may help to prevent any of the light 134 which is specularly reflected from the reference photodiode 102 from possibly reaching the sensor photodiode 122.

This may be important since such specularly reflected light 134 may be as much as 1,000 times more intense than the sensor modulated return light 47 which reaches the sensor photodiode 122. Thus, it may be critical that such specularly reflected light 134 not be permitted to reach the sensor photodiode 122, where it might give rise to significant measurement errors in the sensor electrical signal from the sensor photodiode 122.

The secondary optical-electrical circuit 133 may serve two purposes simultaneously. First, it may provide a reference electrical signal at the electrical connector 104. Second, it may act as an efficient two-step light dump for all of the reflected light 134 from the dichroic filter 116. That is, essentially all of the reflected light 134 may be absorbed by either the reference photodetector 102, or by the layer of light absorbing material 100.

Let it now be assumed, by way of example, that the excitation light 34 and the sensor modulated return light 47 are of different wave bands (as may be the case if the sensor 20 is selected to be an evanescent wave excited, fluorescence light-generating type of intrinsic sensor 20); and let it now be further assumed that the sensor 20 is simultaneously designed to permit a small amount of the excitation light 34 which enters the sensor 20 to be reflected back to the light receiver module 26 through the sensor fiber 76, the array of light return fibers 46, and the receiver optical fiber 94.

Thus, in such a case, the receiver module 26 may receive a mixture of light of two different wave bands from the sensor 20, namely a sensor wave band and a reference wave band. The sensor wave band may comprise sensor modulated return light 47; and the reference wave band may comprise excitation light 34.

It may be important to note that both the light in the sensor wave band, as well as the light in the reference wave band, may have traveled the same path through the multifunctional sensor system 10, i.e, sequentially through the sensor 20, the sensor fiber 76, the array of return fibers 46, and the receiver optical fiber 94.

The sensor 20 may be designed to reflect back a small amount of the excitation light 34 to the light receiver module 26 through the sensor fiber 76, the array of light return fibers 46, and the receiver optical fiber 94 in any suitable way. This may be done, for example, by providing an imperfect light dump at the distal end of the sensor 20's sensing fiber, to intentionally permit some of the left-over excitation light 34 to be reflected back by the sensor 20.

Another suitable way may be to incorporate a diffuse scattering media in the sensor 20's sensing fiber, to produce diffuse backscatter of the excitation light 34 from the sensor 20. This may be relatively easy to do if the sensor 20's sensing fiber comprises a plastic, rather than a glass. This may be because the scattering media (such as small quartz, alumina or titanium dioxide particles) may be simply mixed into the raw polymer before the sensor 20's sensing fiber is injection molded or extruded from the polymer/scattering media mixture.

A further suitable way may be to intentionally roughen the surface of the sensor 20's sensing fiber, so that the roughened surface may produce diffuse backscatter of the excitation light 34 from the sensor 20 into the sensor fiber 76, the array of light return fibers 46, and the receiver optical fiber 94. Such roughening may be done in any appropriate way, such as by lightly etching the outer surface of the sensor 20's sensing fiber.

Another suitable way may be to add a reflective coating to the surface and/or to the distal end of the sensor 20's sensing fiber, so that the sensor 20 may reflect some of the excitation light 34 back into the sensor fiber 76, the array of light return fibers 46, and the receiver optical fiber 94.

Alternatively, the sensor 20 may be provided with a coating of two different fluorophores which fluoresce at two different wave bands. The fluorophores may be selected such that a first, sensor fluorophore fluoresces in a first, sensor wave band in the presence of the target chemical when stimulated by the excitation light 34; while a second, reference fluorophore fluoresces in a second, reference wave band when stimulated by the excitation light 34. The reference fluorophore may fluoresce in the presence of the target chemical; or it may continuously fluoresce when stimulated by the excitation light 34, whether or not the target chemical may be present.

The molecules of the sensor fluorophore and the reference fluorophore may be immobilized on the surface of the sensor 20's sensing fiber in any suitable way. For example, this may be done by using the same kind of linking molecule to bond both the reference fluorophore and the sensor fluorophore to the surface of the sensor 20's sensing fiber. This may be done by first chemically bonding the needed sensor and reference fluorophores to the linking molecules (such as by adding the needed sensor and reference fluorophores to a solution containing the linking molecules); and by then immersing the sensor 20's sensing fiber in the resulting solution so that the linking molecules may then immobilize the sensing and reference fluorophores on the surface of the sensing fiber.

Alternatively, the reference fluorophore may be chemically bound to the molecule containing the sensing fluorophore; which may, in turn, be immobilized on the surface of the sensing fiber in any suitable way, such as by using a surface linking molecule, a surface immobilized antibody, a bound molecular fragment, or other molecular entity.

Alternatively, the sensor 20's sensing fiber itself may comprise the second, reference fluorophore. For example it may comprise a material which naturally fluoresces when stimulated by the excitation light 34, such as a high NA plastic; or it may be doped with the second fluorophore.

Here again, it may be important to note that both the sensor and reference wave bands of fluorescent light may have traveled the same path through the multifunctional sensor system 10, i.e., through the sensor 20, the sensor fiber 76, the array of light return fibers 46, and the receiver optical fiber 94.

For any particular fluorophore, the Stokes shift is the difference between the wavelength of the excitation light 34 and the wavelength of peak fluorescence within the band of wavelengths emitted by that particular fluorophore when it is stimulated by the excitation light 34.

In general, it may be desirable for the Stokes shifts of the first, sensor fluorophore and the second, reference fluorophore to be as different as possible, in order to provide maximum separation of the sensor wave band of the sensor modulated return light 47 (which carries information regarding the target chemical), from the reference wave band of the reference fluorescence light. If this occurs, then the sensor wave band and the reference wave band may be more easily separated spectrally.

It may be acceptable, or even preferable, to use for the reference fluorophore one which may have a relatively small Stokes shift, while the sensor fluorophore may be selected to have a relatively large Stokes shift; in order to obtain the maximum separation of the sensor wave band from the reference wave band. Thus, if the excitation light 34 has a wavelength which is far beyond the peak fluorescence emission wavelength of the reference fluorophore, the reference fluorophore may only emit fluorescence light in a small wave band extending beyond the wavelength of the excitation light 34.

For example, if the excitation light has a wavelength of 635 nm, the compound cresyl violet perchlorate may be suitable for a small Stokes shift reference fluorophore since its peak absorbance wavelength is at 593 nm, and yet measurable fluorescence may be obtained up to a wavelength of about 640–700 nm.

In general, there are many more low Stokes shift fluorophore options than there are high Stokes shift fluorophores, so selection of a suitable reference fluorophore may generally not pose a problem. The larger issue may be the limited number of sites on the sensor 20's sensing optical fiber which may be available for use for sensing purposes versus reference purposes.

Similarly, when there is only one fluorophore, the sensor fluorophore, and the reference wave band comprises excitation light 34, it may also be desirable for the sensor fluorophore to have a relatively large Stokes shift. This may be desirable in order to provide maximum separation of the sensor wave band of the sensor modulated return light 47 (which carries information regarding the target chemical), from the reference wave band of the reference excitation light 34; which may permit the sensor wave band and the reference wave band to be easily separated spectrally.

From all of the forgoing it should now be clear that the light entering the light receiver module 26 through its receiver optical fiber 94 may be a mixture of two different wave bands, i.e., a sensor wave band and a reference wave band. The sensor wave band may comprise the sensor modulated return light 47. The reference wave band may comprise a portion of the excitation light 34, or it may comprise reference fluorescence light. The light received by the receiver module 26 in both the sensor wave band and the reference wave band may have travelled the same path through the multifunctional sensor system 10, i.e., through the sensor 20, the sensor fiber 76, the array of light return fibers 46, and the receiver optical fiber 94.

Turning again to FIG. 15, the dichroic filter 116 may be selected to pass only the sensor wave band, and to reflect the reference wave band through the secondary optical-electrical circuit 133 to generate a reference electrical signal at the electrical connector 104.

The receiver module 26 may further comprise any conventional means (not illustrated, for clarity), for taking the ratio of the sensor electrical signal and the reference electrical signal, and then generating a ratiometric output electrical signal from them, to null certain errors which might otherwise be generated in the multifunctional sensor system 10.

For example, if the reference electrical signal at the electrical connector 104 is generated by excitation light 34 which has been reflected back from the sensor 20, it can be shown that the reference electrical signal's photocurrent, $I_r$, is proportional to the product of the intensity of the excitation light 34, $I_o$; the reflectivity, R, of the sensor 20 at the wavelength of the excitation light 34; the transmission, $\tau$, of the array of return light fibers 46; and a proportionality constant, $g_r$, that is less than 1:

$$I_r = g_r I_o R \tau \qquad \text{Equation 2}$$

The photocurrent of the sensor electrical signal at the wires 126, $I_s$, is proportional to the product of the intensity of the excitation light 34, $I_O$; the fluorescence signal strength, f, per unit excitation and per unit concentration of the target chemical; the concentration, [C], of the target chemical; the transmission, $\tau$, of the array of return light fibers 46; and a proportionality constant, $g_s$, that is less than 1:

$$I_s = g_s I_o f[C]\tau \qquad \text{Equation 3}$$

The ratio, I*, of $I_r$ and $I_s$, is then:

$$I* = \left(\frac{g_s f}{g_r R}\right)[C] \qquad \text{Equation 4}$$

From the above Equation 4 it is seen that the ratiometric signal, I*, is now independent of the intensity of the excitation light 34, $I_o$, and the transmission, $\tau$, of the array of return light fibers 46. Instead, the ratiometric signal, I*, is dependent only on the concentration, [C], of the target chemical, and on the design parameter ($g_sf/g_rR$) of the multifunctional sensor system 10.

It is worth noting again that in order for the above ratiometric signal, $I^*$, to be independent of certain parameters, as set forth above, it may be important for both the light in the sensor wave band (which generated the sensor photocurrent, $I_s$), and the light in the reference wave band (which generated the reference photocurrent, $I_r$), to have traveled similar paths through the sensor 20, the sensor optical fiber 76, the array of return light fibers 46, and the receiver optical fiber 94.

Figure 16:
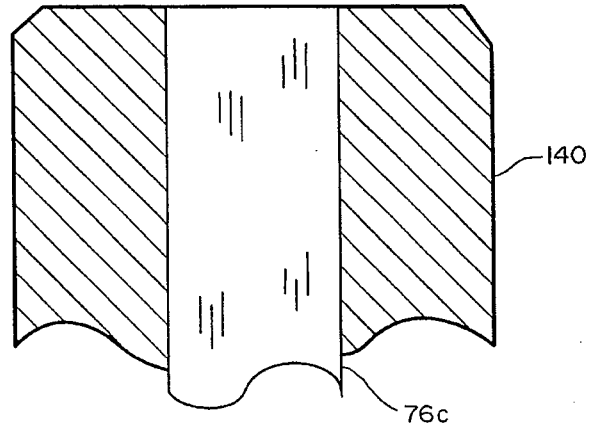
FIG. 16 is a diagrammatic top elevational view, partly in cross section, of the interface between a fourth embodiment of the sensor connector's sensor optical fiber, and a fourth embodiment of the sensor interface connector's optical fiber bundle comprising an excitation fiber and an array of return light fibers.

Referring now to FIG. 16, it illustrates another embodiment of the optical fiber bundle 70c, which may be carried by the sensor interface connector 18's pin 48. FIG. 16 also shows the sensor connector 72's pin 140 with its sensor optical fiber 76c.

The optical fiber bundle 70c may comprise an excitation fiber 40c, and an array of angled return light fibers 46c. The angled return fibers 46c may be located in the connector pin 48 in any suitable way, such as by drilling suitable holes in the connector pin 48 for them. Alternatively, a cone-shaped hole may be drilled in the connector pin 48, and the return fibers 46c may then be potted in place with epoxy along the angled sides of the cone-shaped hole.

All of the comments made above regarding the excitation fiber 40, the array of return fibers 46, and the sensor fiber 76, of FIGS. 6, 8 and 9–9A apply equally well to the excitation fiber 40c, the array of return fibers 46c, and the sensor fiber 76c of FIG. 16, except for those differences which may be made expressly or inherently apparent from all of the disclosures herein.

It is well known that the angular distribution of the sensor modulated return light 47 emanating from an evanescent wave excited, fluorescence light-generating type of intrinsic sensor 20 may be very large, encompassing a high NA. This may be because excited fluorophore molecules may generally emit fluorescence light isotropically, requiring the sensor optical fiber 76c to transport a large number of "leaky modes", of the sensor modulated return light 47.

As was discussed above regarding FIGS. 13 and 14, if the sensor fiber 76c has a circular cross-section, about 70% of the sensor modulated return light 47 may be concentrated in an annular zone extending over the outer 20% of the sensor fiber 76c's cross-section.

On the other hand, if the sensor optical fiber 76c has a non-circular cross-section, it may generate power distributions of the sensor modulated return light 47 which are non-uniform and unsymmetric over the end face of the sensor fiber 76c.

It has been discovered that an array of return fibers 46c may be used to optimally couple signal energy from either a circular or a non-circular sensor fiber 76c by: (a) tilting the array of return light fibers 46c with respect to the longitudinal axis of the sensor fiber 76c, and making their end faces parallel to the end face of the sensor fiber 76c; and/or (b) positioning the end faces of the return light fibers 46, 46a, 46b, 46c to coincide with the portions of the end face of the sensor fiber 76c which carry high intensities of the sensor modulated return light 47.

Option (a) above may be of particular value if the return fibers 46c have a low NA. Although, in general, high NA return fibers 46c may be preferable for recovery of the sensor modulated return light 47, low NA return fibers 46c may be preferred if the distance between the sensor 20 and the light receiver module 26 is great, since high NA fibers typically exhibit high loss per unit length.

Preferably, the position and tilt angle of the return fibers 46c may be selected to correspond spatially and in angle to any peaks in the distribution of energy emanating from the end of the sensor fiber 76c.

However, if the sensor fiber 76c is emanating sensor modulated return light 47 with a spatially-symmetric far-field pattern, there may be no benefit to tilting the return fibers 46, since gains in one direction may be matched by losses in the opposing direction.

It is well recognized that conventional evanescent wave excited, fluorescence light-generating type of intrinsic sensors 20 may be relatively inefficient fluorescence light capture devices due to the isotropic nature of their fluorescence emissions. They may also be relatively inefficient fluorescence light capture devices because of NA limitations within their sensing fibers, within portions of their sensing fibers which are not bathed in the liquid containing the target chemical, or within the sensor fiber 76c which connects the sensor 20's sensing fiber to the sensor connector 72.

In fact, a typical conventional evanescent wave excited, fluorescence light-generating type intrinsic type of sensor 20 may only recover about 1%–10% of the fluorescence light which is emitted from the surface of such a sensor 20's sensing fiber.

Since only sensor modulated return light 47 travelling down the sensor 20 in the direction of sensor connector 72 may be captured by the array of return light fibers 46, the light capture efficiency of the array of return light fibers 46 may not exceed 50%.

This problem may be further exacerbated if the fluorophores on the sensor 20's sensing fiber do not electromagnetically couple with the sensing fiber. This is because in such a case the fluorescence light emitted by the fluorophores may pass though the sensing fiber and exit in a mirror-image fashion from the opposite side of the sensing fiber, even if the fluorescence light is potentially within the sensing fiber's capture angle.

Turning now to FIG. 17, it illustrates an improved evanescent wave excited, fluorescence light-generating type of intrinsic sensor 142, with its associated fiber bundle 70d. The fiber bundle 70d may comprise an excitation fiber 40d and an array of return light fibers 46d.

The theory, structure and operation of the sensor 142, with its fiber bundle 70d, of FIG. 17 may be the same as, or similar to, the theory, structure and operation of the sensor 20, with its fiber bundles 70, 70c; of FIGS. 6, 8, 9–9A and 16, except for those express or inherent differences which may be made apparent by all of the disclosures herein.

The sensor 142 may comprise a sensing fiber 144, having a coating of fluorophore(s) on its outer surface 146, which may be selected to fluoresce in the presence of the target chemical, when stimulated by the excitation light 34. The sensor 142 may further comprise an annular sample chamber 148 which may be filled with the sampled fluid 149 which is to tested for the presence of the target chemical.

The annular sample chamber 148 may be defined between the sensing fiber's outer surface 146 and the inner surface 150 of an annular waveguide 152. The annular waveguide 152 may have annular left and right faces 154, 156; and may have an outer surface 157 which may be either cylindrical or tapered. If tapered, it may be tapered in any suitable way, such as by dipping a cylindrical annular waveguide 152 vertically into a suitable etchant, and then withdrawing it from the solution at a rate sufficient to impart the desired amount of taper to the annular waveguide 152. Alternatively, a cylindrical annular waveguide 152 may be heated to its softening point, and then stretched, until the desired degree of taper has been obtained. The annular waveguide 152 may comprise any suitable material, such as a 10 cm length of conventional glass or quartz capillary tubing.

If the waveguide 152 has a tapered outer surface 157, only the portion of its outer surface which overlies its sample chamber 148 may be tapered. The rest of the waveguide 152's outer surface may be cylindrical, rather than tapered.

Spacing between the sensing fiber 144 and its surrounding annular waveguide 152 may be provided in any suitable way, such as by the use of a slotted annular tube located therebetween, The annular waveguide 152 may serve triple purposes, i.e., forming the outer wall of the sample chamber 148; wave guiding light in the sensor wave band; and/or wave guiding light in the reference wave band.

Fluid samples containing the target chemical may be introduced into the sample chamber 148 in any suitable way. For example, they might be introduced into the left end of the sample chamber 148 by using a pressurized sample source, surface tension priming, immersion, or a combination thereof.

Flow of fluid samples through the sample chamber 48 may be provided in any suitable way. For example, an annular ring 153 of low refractive index optical elastomer, having one or more axial holes 155, may be provided in the right end of the sample chamber 148. Such axial holes may act as a vent, an inlet or an outlet for the sample chamber 148.

Alternatively, one or more radial holes may be drilled (as with a laser or an ultrasonic drill), through the annular waveguide 152 to the sample chamber 148. Such radial holes may act as vents, inlets or outlets for the sample chamber 148. However, care may have to be taken to minimize loss of the sensor modulated return light 47 at such radial holes, such as by etching the inner and/or outer surfaces 152, 157 of the annular waveguide 152 clean after the laser drilling, or by coating those surface(s) with a low NA material.

Alternatively, the excitation fiber 40d may be made from a hollow capillary tube, and the longitudinal bore of such a capillary tube may be used as a vent for the sample chamber 148. Fluid communication between the sample chamber 148 and the interior of such a hollow excitation fiber 40d may be provided in any suitable way, such as by laser-drilling one or more radial holes in the sidewall of the hollow excitation fiber 40, or by providing a suitable axial hair-pin flow loop.

Since the annular waveguide 152 may not be required to transport any excitation light 34, the materials from which it is made may be selected for other factors such as high NA and low cost, for example. Both transparent glasses and plastics may be acceptable in this regard. Since the improved sensor 142 may be on the order of 10 cm, or less, in length, materials with a comparatively high optical absorbance may be used for the annular waveguide 152, because of the short path travelled by the sensor modulated return light 47 within the waveguide 152. It may also be possible to operate the annular waveguide 152 with air over at least a majority of its outer surface, thereby creating a very high NA multifunctional sensor system 10. For example, if such an air-exposed annular wave-guide 152 was made from quartz, its NA may approach 1.0.

In some cases, the annular waveguide 152 may be dyed with a material that may preferentially absorb light at the wavelength of the excitation light 34, thereby improving the signal to noise ratio of the sensor modulated return light 47 transmitted from the sensor 142 to the light receiver module 26.

The sensor 142's sensing fiber 144 may preferably have a diameter which is at least as great as the diameter of the excitation fiber 40d, for better transfer of the excitation light 34 from the excitation fiber 40d to the sensing fiber 144; although the sensing fiber 144 may be smaller in diameter than the excitation fiber 40d.

During operation, the excitation light 34 which is injected into the sensing fiber 144 by the excitation fiber 40d may cause the fluorophores on the sensing fiber 144's outer surface 146 to fluoresce, if the target chemical is present in the sampled fluid 149 in the annular sample chamber 148. The fluorescence light may be intentionally allowed to escape from the sensing fiber 144, so that it may then be trapped by the annular waveguide 152, which surrounds the sensing fiber 144 and the annular sample chamber 148.

The improved sensor 142 may capture as much as about 25% of the fluorescence light which is emitted from the surface of the sensor 142's sensing fiber 144—a remarkable improvement over the performance of conventional intrinsic sensors 20 which do not have an annular waveguide 152; and, which, as was mentioned above, may capture only about 1%–10% of the fluorescence light which their sensing fibers emit.

The outer surface 157 of the annular waveguide 152 may be either cylindrical or tapered. Tapering the outer surface 157 may allow the designer some control over the angular characteristics of the sensor modulated return light 47. A tapered outer surface 157 may, as seen in FIG. 17, cause a ray of the sensor modulated return light 47 to travel more nearly parallel to the longitudinal axes of the return light fibers 46d with each reflection from the waveguide 152's outer surface 157.

A tapered outer surface 157 on the annular waveguide 152 may result in high NA signal light being converted into lower NA light as return light 47 travels towards the return fibers 46d. This may mean that lower NA fibers may be used for the return fibers 46d, with no loss in signal due to an overfilled NA; which may result in the sensitivity of the multifunctional sensor system 10 being improved overall as compared to if lower NA fibers were used when the outer surface 157 was not tapered.

If the taper is present along the entire outer surface 157 of the annular waveguide 152, then tapers as small as one degree, or less, may be useful in reducing high NA fluorescence light into lower NA fluorescence light. Where space or other limitations indicate that a short tapered "impedance matching" zone between the sensing fiber 144 and the fiber bundle 70d, is better, then linear tapers of up to 10°–15° may be acceptable, Typically, a long, gradual taper will be more efficient that a short, sharp-angled taper.

In addition, the annular left end face 154 of the waveguide 152 may be metallized, or mirrored, so that any sensor modulated return light 47 which may initially travel towards the left end face 154, may be reflected back towards the array of return light fibers 46d at the right end face 156. This may result in nearly 100% of the fluorescence light emitted by the sensing fiber 144 to be captured by the annular waveguide 152 and transferred to the return light fibers 46—a remarkable improvement over the performance of the conventional evanescent wave excited, fluorescence light-generating type of sensors 20 mentioned above.

Further, the sensor 142 may also significantly reduce concerns regarding electromagnetic coupling at the annular waveguide 152's inner surface 150.

It may not be practical in all cases to use air as the annular waveguide 152's cladding. If this is the case, in order to maximize the amount of sensor modulated return light 47 which may be delivered by the waveguide 152 to the return fibers 46d, the waveguide 152's external surface may be coated with standard low refractive index polymers used for plastic-clad fiber optics, most principally compounds in the silicone and fluorocarbon classes, or evaporated metals and/or sputtered layers of low refractive index dielectrics such as magnesium fluoride.

Since the excitation light 34 may not intentionally enter or excite the annular waveguide 152, there may be less excitation light 34 corrupting the sensor modulated return light 47, allowing detection of very low-levels of sensor modulated return light 47.

There may be several return light fibers 46d, for conveying the sensor modulated return light from the sensor 142 to the light receiver module 26. Preferably, as seen in FIG. 17, the end faces 158 of the return light fibers 46d are located opposite, and adjacent to, the waveguide 152's right annular end face 156, although portions of the end faces 158 may extend radially inwardly or radially outwardly past the end face 156. The number and diameters of the return light fibers 46d may be selected such that their end faces 158 cover as much of the waveguide 152's right annular end face 156 as possible, for better transfer of the sensor modulated return light 47 from the sensor 142 to the array of return light fibers 46d. All of the return light fibers 46d may not be of the same diameter.

The fiber bundle 70d may be held in the sensor interface connector 18's pin 48; while the annular waveguide 152 may be elongated, so that its right end portion and its right end face 156 may be held in the sensor connector 72.

Alternatively, the return light fibers 46d may be arranged opposite, and adjacent to, the waveguide 152's annular left end face 154, instead of opposite its annular right end face 156. In such a case, instead of metalizing, or mirroring, the annular left end face 154, the annular right end face 156 may be metallized, or mirrored, so that any sensor modulated return light 47 which may initially travel towards the right end face 156, may be reflected back towards the array of return light fibers 46d opposite the left end face 154. In such a case, the annular waveguide 152 may also be elongated, so that its left end portion and its left end face 154 may be held in the sensor connector 72.

Turning now to the sensor 142a and its fiber bundle 70f of FIG. 17A, their theory, operation, structure and manufacture may be the same as, or similar to, the theory, operation, structure and manufacture of the sensor 142 and fiber bundle 70d of FIG. 17, except for those express or inherent differences which may be made apparent by all of the disclosures herein.

As seen in FIG. 17A, the annular sample chamber 148 may be eliminated; and the inner surface 150a of the waveguide 152a may be close to, or in contact with, the outer surface 146a of the sensing fiber 144a. In such a case, the annular waveguide 152a may be made of any suitable porous, permeable or hydrophilic material, such as cellulose, a silicone-based elastomer, or a fluorocarbon, for example, so that it may absorb the target chemical to be tested, and convey it to the outer surface 146a of the sensing fiber 144a. Thus, in order to test a fluid sample for a target chemical, the waveguide 152a may simply be immersed in the fluid sample to be tested.

The sensor 142a of FIG. 17A, in which the annular sample chamber 148 has been eliminated, may be particularly interesting. From a manufacturing standpoint, the layer of the target and/or reference fluorophore(s) 176 may first be placed on the sensing fiber's outer surface 146a in any suitable way, such as by the use of covalent chemical bonding, or dip coating, for example. The annular waveguide 152a may simply comprise a polymer coating that may then be deposited onto the sensing fiber 144a in any suitable way, such as by dip coating, casting, or co-extruding, for example. Thus, the sensor 142a may be unusually simple and inexpensive to manufacture.

Although the annular waveguide 152a is illustrated as having a uniform thickness, it may be tapered in thickness, as was the annular waveguide 152 of the sensor 142 of FIG. 17.

As seen in FIG. 17, in order to minimize back reflection of the excitation light 34 from the sensing fiber 144a's distal end 170, the distal end 170 may be polished to a 45° or sharper, taper, and may have a coating 172 comprising an epoxy or other polymer containing an opacifier or absorber selected to absorb the excitation light 34.

Alternatively, the sensing fiber 144a's distal end 170 may not be tapered, but may, instead, be located in a plane oriented at a right angle with respect to the sensing fiber 144's longitudinal axis; and/or it may be provided with a reflective coating, in order to reflect the excitation light 34 back towards the excitation fiber 40f.

It has been discovered that this may effectively double the amount of sensor modulated return light 47 generated by the sensing fiber 144a (and may thus double the sensitivity of the sensor 142a), particularly where the layer 176 of fluorophore(s) on the surface of the sensing fiber 144a only weakly absorb the evanescent waves generated by the excitation light 34. This may be because any of the excitation light 34 that did not successfully excite the fluorophore(s) on its way towards the sensing fiber 144a's distal end 170, may be reflected back and given a second opportunity to do so.

Similarly, it has also been discovered that the annular waveguide 152a's distal end 174 may also be provided with a reflective coating. The purpose of such a reflective coating may be to reflect back towards the return light fibers 46f the sensor modulated fluorescence return light 47 which was initially emitted by the layer 176 of fluorophore(s) on the sensing fiber 144a's outer surface 146a towards the annular waveguide 152a's distal end 174. This may result in a further doubling of the amount of return light 47 which is delivered by the annular waveguide 152a to the return fibers 46f (and thus, further double the sensitivity of the sensor 142a). The combination of these two doublings may then effectively quadruple the sensitivity of the sensor 142a, a remarkable achievement.

The waveguide 144a may comprise any suitable optical fiber of any suitable diameter, such as, for example, a fiber 200 microns in diameter made from quartz, with a refractive index of about 1.456; made from 7740 Pyrex glass, with a refractive index of about 1.485; made from polystyrene, with a refractive index of about 1.58; or made from sapphire, with a refractive index of about 1.75.

The annular waveguide 152a may comprise any suitable material of any suitable diameter, such as, for example, a silicone polymer layer with an outside diameter of about 600 microns, with a refractive index of about 1.405, for example.

The layer 176 of sensor fluorophore(s) on the sensing fiber 144a's outer surface may comprise any suitable fluorophore capable of emitting fluorescence light in the presence of the target chemical, when excited by the excitation light 34. For example, the sensor fluorophore may comprise tris (3,7-diphenyl1,10-phenanthroline) ruthenium (II) chloride, which is known to fluoresce with an intensity that is inversely proportional to the oxygen partial pressure of a target solvent or solution, and which is known to dissolve in silicone polymer. Thus, such a sensor fluorophore may be suitable for determining oxygen partial pressure.

Similarly, fluorophores may be selected or made that are sensitive to many other industrial or chemical process parameters, such as pH or carbon dioxide. These types of fluorophores may be used in the construction of sensors 142a for these parameters, or associated parameters, such as ammonia. For example, for pH sensing, the annular waveguide 152a may comprise a proton conductor such as, for instance, hydrated cellulose, a polyether, a polyamide, polyacrylic acid, a polyamine, or polyvinyl alcohol.

On the other hand silicone and fluorocarbon based polymers are well suited for gaseous species such as carbon dioxide and oxygen.

It may also be possible to coat the sensing fiber 144a with a thin coating of a metal such as silver or palladium, for example, which may be, for example, less than about 1,000 Å thick. The presence of a target compound such as hydrogen chloride or hydrogen sulfide, for example, would convert the metal to a chloride or a sulfide salt. This change in chemical composition would bring about a dramatic change in the surface optical properties of the sensing fiber 144a, thereby modifying the fluorescence output of a sensing fluorophore that had been coated either on the top of or underneath the metal film, and providing non-reversible sensors for these two target compounds.

Similarly, the palladium film would be reactive towards hydrogen, for example, forming palladium hydride and changing the manner in which excitation light 34 internal to the sensing fiber 144a could access fluorophore deposited onto, or beneath, the palladium. The reaction of palladium with hydrogen is, to some extent, reversible at ambient temperatures; thereby possibly providing a reversible sensor for hydrogen.

In a third embodiment, the sensing fiber 144a may be coated with a fluorophore whose fluorescence output is known to be quenched by the presence of heavy metals. Heavy metal quenching of fluorescent species is a well-known and well-documented phenomenon. The annular waveguide 152a may be composed of a so-called solid polymer electrolyte that is permeable to heavy metal ions. When the annular waveguide 152a is immersed in a solution containing heavy metal ions, the fluorescence output of the sensing fiber 144a would be reversibly quenched by metal ions in solution diffusing into the waveguide 152a and interacting with embedded fluorophores. Suitable solid polymers might include polyethers such as polyethylene oxide-based electrolytes and various types of commercial ion exchange resins.

All such materials which are useful for the sensor 142a may also be used for the sensors 20, 142.

By way of example, if the sensing fiber 144a has a refractive index of 1,456, and if the annular waveguide 152a has a refractive index of 1.405, then the NA of the sensing fiber waveguide 144a may be about 0,382 and the NA of the composite waveguide 144a, 152a may be about 0.444, if the annular waveguide 152a is immersed in water. On the other hand, if the annular waveguide 152a is immersed in air, then the NA of the composite waveguide 144a, 152a may be about 0.98.

During operation of the sensor 142a, the excitation fiber 40f may inject the excitation light 34 into only the sensing fiber 144a. The material from which the annular waveguide 152 is made may be selected to comprise a material that is lower in refractive index than the material from which the sensing fiber 144a is made. This may result in the desirable fact that the excitation light 34 may only be transported within the sensing fiber 144, and not within the annular waveguide 152.

The sensor modulated return light 47 which may be generated by the layer 176 of fluorophore(s) on the surface of the sensing fiber 144a, under the stimulation of the excitation light 34, may now be captured by the compound waveguide 144a, 152a with an efficiency that may be dominated by several factors. The first factor is the refractive indices of the annular waveguide 152a and the surrounding media (such as water or air, for example), since this factor regulates loss of the sensor modulated return light 47 from the compound waveguide 144a, 152a. The second and third factors may be the refractive indices and cross-sectional areas of the sensing fiber 144a and the annular waveguide 152a. These last two factors regulate the distribution of the optical signal power of the sensor modulated return light 47 carried by the compound waveguide 144a, 152a.

The sensor modulated return light 47 captured by the annular waveguide 152a, and traveling towards the fiber bundle 70f's return light fibers 46f, may then be captured by the return light fibers 46f. To maximize the efficiency with which the return light fibers 46f capture the return light 47, it has been discovered that it may be preferable for the sensing fiber 144a's cross-sectional area to be smaller than the cross-sectional area of the annular waveguide 152a, since this may minimize loss of the return light 47 from the annular waveguide 152a to the excitation fiber 40f at the interface between the sensor 142a and the fiber bundle 70f.

From the forgoing, it will be appreciated that the sensor 142a may be made considerably more sensitive than other conventional designs for intrinsic sensors 20.

Figure 17B:
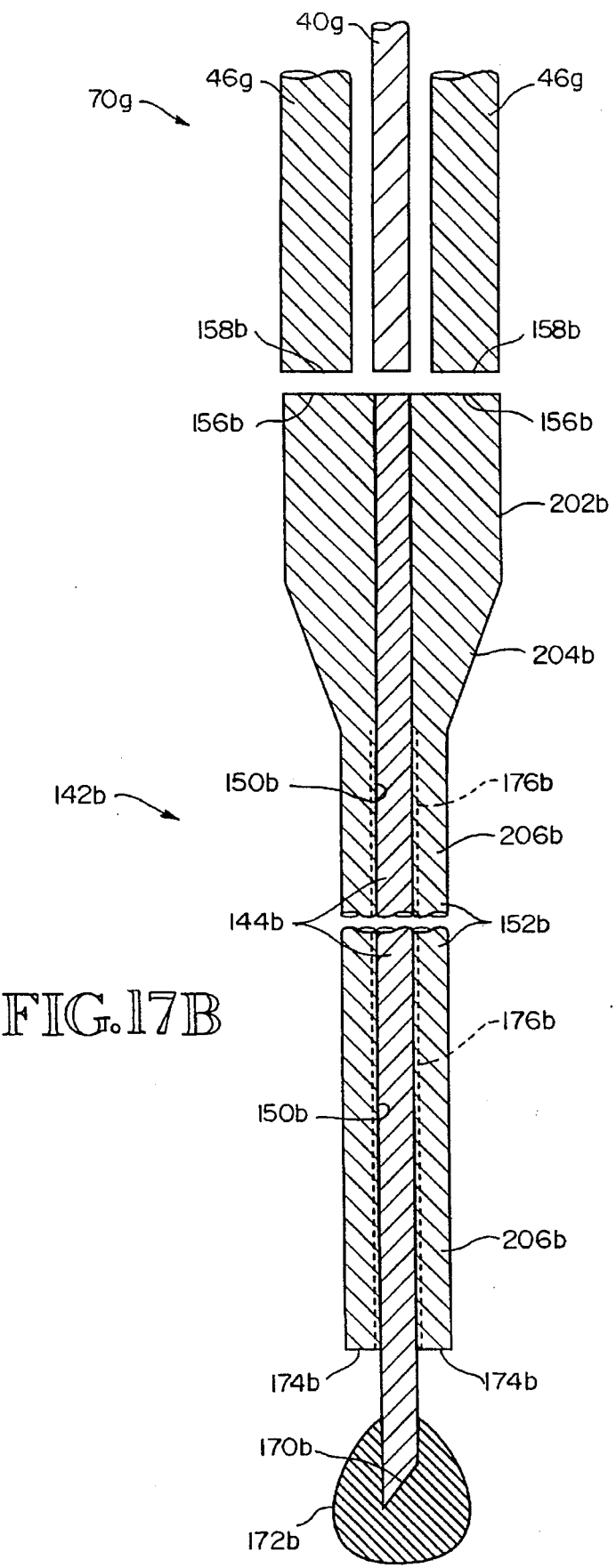
FIG. 17B is longitudinal cross-sectional view of a further embodiment of the annular waveguide optical sensor of the present invention.

Turning now to the sensor 142b and its fiber bundle 70g of FIG. 17B, their theory, operation, structure and manufacture may be the same as, or similar to, the theory, operation, structure and manufacture of the sensor 142a and its fiber bundle 70f of FIG. 17A, except for those express or inherent differences which may be made apparent by all of the disclosures herein.

The annular waveguide 152b may comprise an annular sensor optical fiber 202b, an annular transition optical fiber 204b, and an annular waveguide portion 206b which covers the sensing fiber 144b. The theory, operation, structure and manufacture of the elements 202b, 204b, 206b of FIG. 17B may be the same as, or similar to, the theory, operation, structure and manufacture of the corresponding elements 202, 204, 206, respectively, of the sensor 200 of FIGS. 18–20, except for those express or inherent differences which may be made apparent by all of the disclosures herein.

As seen in FIG. 17B, the end faces of the return light fibers 46g may be located so as to receive the sensor modulated return light 47 from those areas of the end face of the annular sensor fiber 202b which may be particularly rich in the return light 47.

Figure 18:
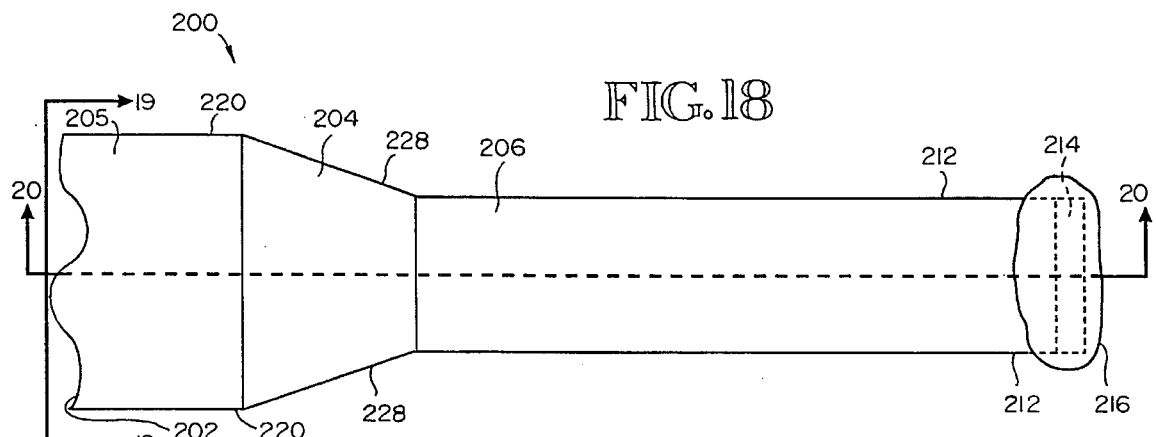
FIG. 18 is a top elevational view of the ribbon-shaped waveguide embodiment of the optical sensor of the present invention.
Figure 20:
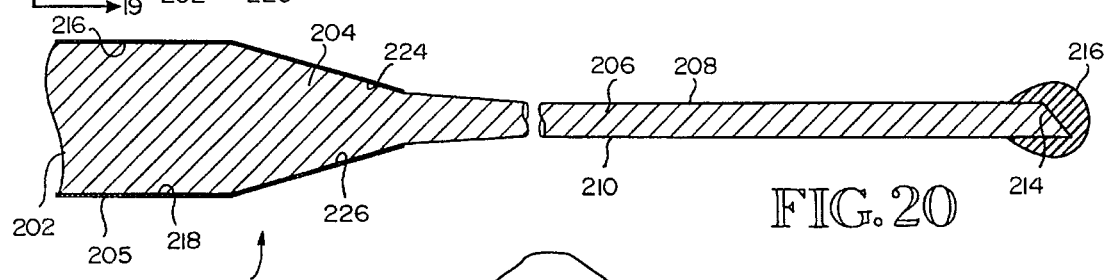
FIG. 20 is a longitudinal cross-sectional view, taken along line 20—20 of FIG. 18.
Figure 19:
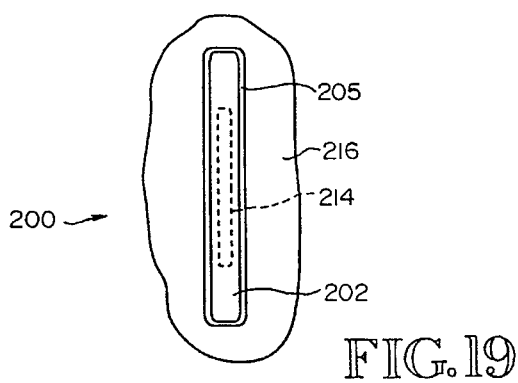
FIG. 19 is an end elevational view, taken along line 19—19 of FIG. 18.

Turning now to FIGS. 18–20, virtually all multimode intrinsic optical fiber sensor development has focused on intrinsic optical fiber sensors 20 using an optical sensing fiber which comprised an optical waveguide having cylindrical symmetry. This may be due in a large part to the relatively recent perfection and commercial acceptance of low-loss cylindrical optical fibers for telecommunications applications.

However, it has been discovered that the use of an array of return light fibers 46–46g to recover the sensor modulated return light 47 from the sensor 20's sensor fiber 76, which was described above, may allow the construction of an improved sensor 20 having a sensing fiber which comprises an optical waveguide having non-cylindrical symmetry. It has been further discovered that such an improved sensor 20 may have a performance which is comparable to, or even superior to, the performance of sensors 20 having a cylindrical sensing fiber.

One form of such an improved intrinsic optical fiber sensor 200 is illustrated in FIGS. 18–20. The sensor 200 may be particularly useful as an evanescent wave excited, fluorescence light-generating type of intrinsic optical fiber sensor 200. The theory, structure and operation of the sensor 200 may be the same as, or similar to, the theory, structure and operation of the sensor 20, except for those differences which will be expressly or inherently made apparent from all of the disclosures in this document.

The sensor 200 may comprise a sensor optical fiber 202, a transition optical fiber 204, and a sensing optical fiber 206. As seen in FIGS. 18–20, the fibers 202, 204, 206 may not be discrete fibers, but may, instead, be different portions of one optical fiber. The sensor fiber 202 and the transition fiber 204 may have a cladding 205 of a low refractive index material, such as a silicone or a fluorocarbon; a reflective metal; or a low refractive index inorganic compound such as magnesium fluoride.

As best seen in FIGS. 18 and 20, the sensing fiber 206 may be generally ribbon-shaped; may have a generally rectangular cross-section; and may have a top surface 208, a bottom surface 210 and a pair of side surfaces 212. Although the top, bottom and side surfaces 208, 210, 212 are illustrated as being flat, they may not be perfectly flat, but may be concave, convex, or may have a more complex shape.

The intersections of the top and bottom surfaces 208, 210 with the side surfaces 212 may be curved, or radiused, rather than sharp cornered, reflecting manufacturability issues and a desire to have the sensing fiber 206 interact with rays of excitation light 34 in a well-characterizable way. In addition, the side surfaces 212 may not be flat, but may be curved, or radiused, for similar reasons. For example, if the side surfaces 212 have a height of "t", the side surfaces 212 may have semi-circular cross-sectional configurations with radii of "t/2".

As best seen in FIG. 20, in order to minimize back reflection of the excitation light 34 from the sensing fiber 206's distal end 214, the distal end 214 may be polished to a 45°, or sharper, taper, and may have a coating 216 comprising an epoxy or other polymer containing an opacifier or absorber selected to absorb the excitation light 34.

The sensing fiber 206 may be coated with a layer of sensing and/or reference fluorophores, similar to those described above with respect to the sensor 20.

As seen in FIGS. 18–20, the sensor fiber 202 may have a generally rectangular cross-sectional configuration; with top and bottom surfaces 216, 218, and a pair of side surfaces 220. Although the top, bottom, and side surfaces 216, 218, 220 are illustrated as being flat, they may not be perfectly flat, but may be concave, convex, or may have a more complex shape. The intersections of the top and bottom surfaces 216, 218 with the side surfaces 220 may be curved, or radiused, rather than sharp cornered, reflecting manufacturability issues and a desire to have the sensor fiber 202 interact with rays of excitation light 34 in a well-characterizable way. In addition, the side surfaces 220 may not be flat, but may be curved, or radiused, for similar reasons. For example, if the side surfaces 220 have a height of "t", the side surfaces 220 may have semi-circular cross-sectional configurations with radii of "t/2".

As best seen in FIGS. 18 and 20, the transition fiber 204 may have a generally pyramidal shape; with top and bottom surfaces 224, 26, and a pair of side surfaces 228 which taper from their respective sensor fiber surfaces 208, 210, 212, to their respective sensing fiber surfaces 216, 218, 220.

It has been discovered that the taper in the transition fiber 204 may provide two potential advantages. First, the taper may act as an impedance transforming element, converting the modal characteristics of the excitation light 34 in sensor fiber 202 to be more compatible with the modal characteristics required to efficiently interrogate the sensing fiber 206's layer of fluorophores. This process will generally consist of increasing the NA range of the excitation light 34.

The second advantage of the taper in the transition fiber 204 may be that it may down shift the angular distribution of the sensor modulated return light 47 sent from the sensing fiber 206 to the sensor fiber 202 (i.e., transform higher NA sensor modulated return light 47 into lower NA sensor modulated return light 47). This may be particularly true if the sensing fiber 206 is an evanescent wave excited, fluorescence light-generating intrinsic sensing fiber 206.

Although the transition fiber's top, bottom and side surfaces 224, 226, 228 are illustrated as being flat, they may not be flat, but may be concave, convex, or may have a more complex shape. For example, the surfaces 224, 226, 228 may have a shaped reflection profile selected to maximize transfer of the excitation light 34 from the sensor fiber 202 to the sensing fiber 206; and to maximize transfer of the sensor modulated return light from the sensing fiber 206 to the sensor fiber 202. Such a shaped reflection profile may be, for example, of the nonfocusing type used in conventional compound parabolic concentrators (CPCs).

The intersections between the transition fiber surfaces 224, 226, 228 with their respective sensor fiber surfaces 208, 210, 212 and sensing fiber surfaces 216, 218, 220 may be curved, or radiused, rather than sharp cornered, reflecting manufacturability issues and a desire to have the transition fiber 204 interact with rays of excitation light 34 in a well-characterizable way.

The intersections of the transition fiber top and bottom surfaces 224, 226 with the side surfaces 228 may be curved, or radiused, rather than sharp cornered, reflecting manufacturability issues and a desire to have the transition fiber 204 interact with rays of excitation light 34 in a well-characterizable way. In addition, the side surfaces 228 may not be flat, but may be curved, or radiused, for similar reasons. For example, if the side surfaces 228 have a height of "t" the side surfaces 228 may have semi-circular cross-sectional configurations with radii of "t/2".

Alternatively, the tapered transition fiber 204 may be eliminated, and the sensing fiber 206 may simply comprise an unclad portion of the sensor fiber 202.

If the sensor 200 does not include a tapered transition fiber 204, then the sensor fiber 202 and the sensing fiber 206 may be extruded in one piece by any conventional means from any suitable glass, or from any suitable plastic, such as polymethylmethacrylate, for example.

If the sensor 200 includes a tapered transition fiber 204, then the sensor 200 may be made in one piece by the processes of casting or injection molding; processes which may be particularly suitable for optical polymers. Alternatively, the sensor fiber 202, the transition fiber 204 and/or the sensing fiber 206 may be formed as separate elements which may then be joined together in any suitable conventional way.

Figure 7:
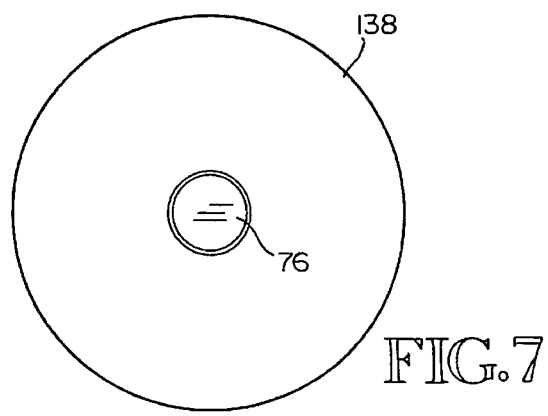
FIG. 7 is an end view of a first form of the connector pin in the sensor connector, taken along line 7—7 of FIG. 4A, having a single, cylindrical, sensor optical fiber.
Figure 7A:
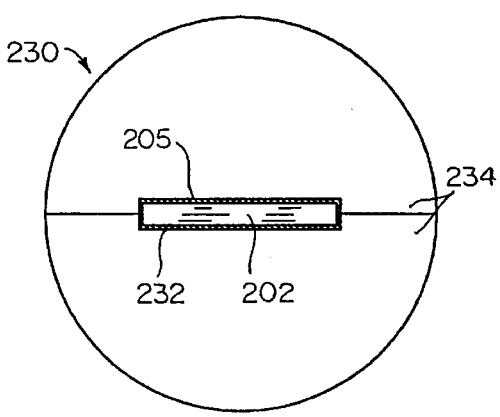
FIG. 7A is an end view of a second form of the connector pin in the sensor connector, taken along line 7A—7A of FIG. 4A, having a single, ribbon-like, sensor optical fiber.
Figure 8:
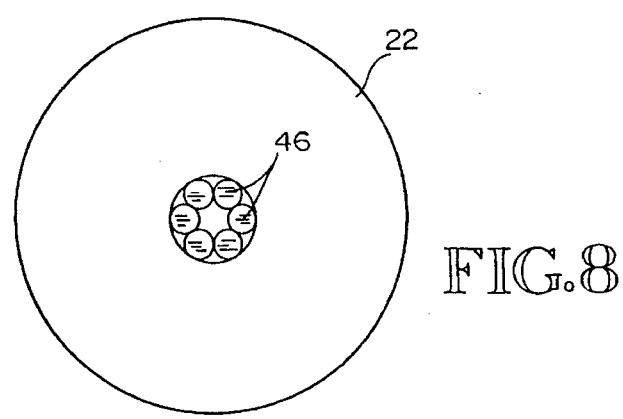
FIG. 8 is an end view of the connector pin in the receiver connector of the return light optical fiber array cable, taken along line 8—8 of FIG. 4.

Turning now to FIG. 7A, the proximal end of the sensor fiber 202 may terminate in the sensor connector 72's connector pin 230. The sensor connector pin 230 may have a rectangular channel 232 sized to receive the sensor fiber 202; and may be split into two halves 234, to permit the sensor fiber 202 to be easily inserted into the channel 232, and then held by the two connector pin halves 234.

Figure 6:
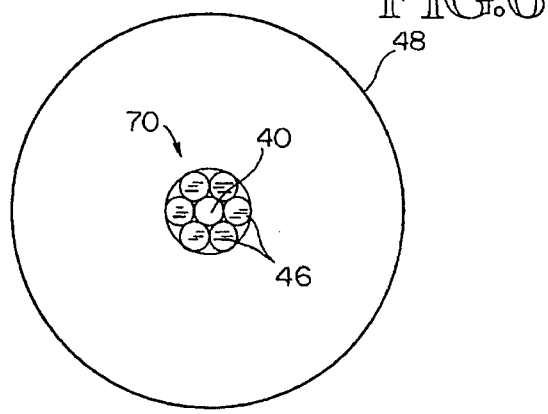
FIG. 6 is an end view of a first form of the connector pin in the sensor interface connector, taken along line 6—6 of FIG. 4A, having an excitation optical fiber centered in an annular array of return light optical fibers.
Figure 6A:
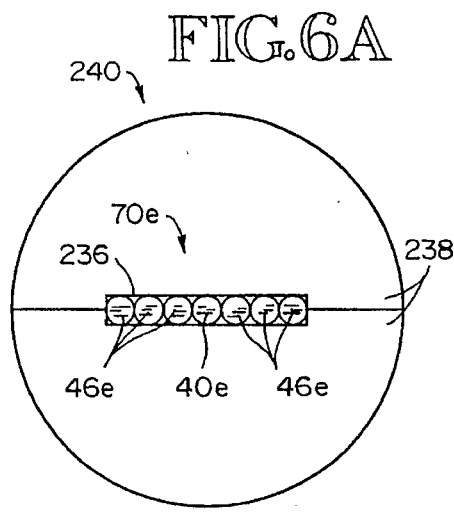
FIG. 6A is an end view of a second form of the connector pin in the sensor interface connector, taken along line 6—6 of FIG. 4A, having an excitation optical fiber centered in a linear array of return light optical fibers.

Turning now to FIG. 6A, the linear fiber bundle 70e may comprise a central excitation fiber 40e, bordered on both sides by an array of return fibers 46e. Although only one, centrally located excitation fiber 40e is illustrated, there may be more than one excitation fiber 40e, and each excitation fiber 40e may not be centrally located. Although the linear fiber bundle 70e is shown having only one row of excitation and return fibers 40e, 46e, there may be more than one row of excitation and return fibers 40e, 46e. Although the diameters of the excitation and return fibers 40e, 46e are illustrated as being equal to the thickness of the sensor fiber 202, they may not be equal.

The fiber bundle 70e may be held in a rectangular channel 236 in the two halves 238 of the connector pin 240 of the sensor interface connector 18.

The sensor interface connector 18 and the sensor connector 72 may be provided with any suitable means, such as keying, to align the linear fiber bundle 70e with the sensor fiber 202.

The excitation fiber 40e, may be located and aligned so as to inject excitation light 34 into a region of the end face of the sensor fiber 202 which may be poor in sensor modulated return light 47. The return fibers 46e may be located and aligned so as to receive the sensor modulated return light 47 from those regions of the sensor fiber 202 which may be rich in the return light 47.

It is to be understood that for any of the sensors 20 described herein, such as those having a sensing fiber 144, 144a or 206, the sensor 20's sensing fiber 144, 144a, 206 may be used in an intensity modulating embodiment of the present invention 10 by incorporating on the sensing fiber 144's, 144a's, 206's surface or within its volume a sensing material that changes the sensing fiber's 144's, 144a's, 206's optical transmission as a function of the target chemical or physical parameter.

For example, the sensing fiber 144, 144a, 206 may be made of a sharp cut filter glass that changes its optical transmission as a function of temperature, such as RG-650 manufactured by Schott Optical Glass Inc. Preferably, the sensing fiber 144's, 144a's, 206's distal end may be made highly reflective in any suitable way.

Alternatively, the sensing fiber 144, 144a, 206 may have a thin layer on its external surface which changes the sensing fiber 144's, 144a's, 206's optical transmission. For example, the thin layer may comprise a metal such as silver or palladium, which may be, for example, less than about 1,000 Å thick. The presence of a target compound such as hydrogen chloride or hydrogen sulfide, for example, would convert the metal to a chloride or a sulfide salt. This change in chemical composition would bring about a dramatic change in the surface optical properties of the sensing fiber 144, 144a, 206, thereby modifying the sensing fiber 144's, 144a's, 206's optical transmission, and providing non-reversible sensors for these two target compounds.

Similarly, the palladium layer would be reactive towards hydrogen, for example, forming palladium hydride This change in chemical composition would bring about a dramatic change in the surface optical properties of the sensing fiber 144, 144a, 206, thereby modifying the sensing fiber 144's, 144a's, 206's optical transmission. The reaction of palladium with hydrogen is, to some extent, reversible at ambient temperatures; thereby possibly providing a reversible sensor for hydrogen.

It is understood that the foregoing forms of the invention were described and/or illustrated strictly by way of non-limiting example.

In view of all of the disclosures herein, these and further modifications, adaptations and variations of the present invention will now be apparent to those skilled in the art to which it pertains, within the scope of the following claims.

What is claimed is:

1. A multifunctional optical sensor system for sensing a sensed target objective, wherein said sensor system comprises:

an optical input means;

an intrinsic optical sensor means comprising an intrinsic optical sensing fiber means; and optical return means;

wherein said optical input means are adapted to receive excitation light from an excitation light source; wherein said optical input means are for conveying said excitation light to said intrinsic optical sensing fiber means;

wherein said intrinsic optical sensing fiber means are for utilizing said excitation light to generate sensor modulated return light as a function of said sensed target objective;

wherein said optical return means are for conveying said sensor modulated return light away from said intrinsic optical sensing fiber means; wherein said optical input means comprises an optical numerical aperture control means, and an excitation optical fiber means; wherein said optical numerical aperture control means is for generating modally controlled excitation light from said excitation light, and is also for delivering said modally controlled excitation light to said excitation optical fiber means; and wherein said modally controlled excitation light received by said excitation optical fiber means is, on the average, less coaxially aligned with a longitudinal axis of said excitation optical fiber means, than would be the case without said optical numerical aperture control means.

2. The multifunctional sensor system according to claim 1, wherein said excitation optical fiber means comprises an input end; and wherein said optical numerical aperture control means comprises an at least generally conical protrusion located near said input end of said excitation optical fiber means.

3. The multifunctional sensor system according to claim 1, wherein said excitation optical fiber means comprises an input end; and wherein said optical numerical aperture control means comprises an at least generally conical pit located near said input end of said excitation optical fiber means.

4. The multifunctional sensor system according to claim 1, wherein said sensor modulated return light comprises sensor modulated fluorescence return light, wherein said intrinsic optical sensing fiber means comprises at least one intrinsic optical sensing fiber having an external surface; wherein said intrinsic optical sensing fiber means further comprises at least one fluorophore on at least a portion of said external surface of said at least one intrinsic optical sensing fiber; wherein said at least one fluorophore emits said sensor modulated fluorescence return light as a function of said sensed target objective when said at least one fluorophore is in the presence of said sensed target objective and is simultaneously stimulated by said modally controlled excitation light; and wherein said modally controlled excitation light is, at least generally, delivered to said excitation optical fiber means by said numerical aperture control means at about the highest possible angle below an escape angle at which said modally controlled excitation light would be lost from said excitation optical fiber means, to tend to maximize the amount of said sensor modulated fluorescence return light which is emitted by said at least one fluorophore in the presence of said sensed target objective, for any given amount of said excitation light emitted from said light source.

5. A multifunctional optical sensor system for sensing a sensed target objective, wherein said sensor system comprises:

an optical input means;

an intrinsic optical sensor means comprising an intrinsic optical sensing fiber means; and an optical return means;

wherein said optical input means are adapted to receive excitation light from an excitation light source; wherein said optical input means are for conveying said excitation light to said intrinsic optical sensing fiber means;

wherein said intrinsic optical sensing fiber means are for utilizing said excitation light to generate sensor modulated return light as a function of said sensed target objective;

wherein said optical return means are for conveying said sensor modulated return light away from said intrinsic optical sensing fiber means; wherein said optical input means comprises at least one excitation optical fiber having an output end with a central portion; wherein said intrinsic optical sensing fiber means comprises at least one intrinsic optical sensing fiber having an interface end with a central portion; wherein said at least one excitation optical fiber is for conveying said excitation light to said at least one intrinsic optical sensing fiber; wherein said central portion of said output end of said at least one excitation optical fiber is at least generally coincident with said central portion of said interface end of said at least one intrinsic optical sensing fiber; wherein said interface end of said at least one intrinsic optical sensing fiber completely overlaps said output end of said at least one excitation optical fiber; and wherein the size of said output end of said at least one excitation optical fiber is up to about 80% of the size of said interface end of said at least one intrinsic optical sensing fiber, to tend to maximize the amount of said excitation light which is conveyed by said at least one excitation optical fiber to said at least one intrinsic optical sensing fiber, despite any lateral misalignment of said central portion of said interface end of said at least one intrinsic optical sensing fiber with respect to said central portion of said output end of said at least one excitation optical fiber.

6. A multifunctional optical sensor system for sensing a sensed target objective, wherein said sensor system comprises:

an optical input means;

an intrinsic optical sensor means comprising an intrinsic optical sensing fiber means; and optical return means;

wherein said optical input means are adapted to receive excitation light from an excitation light source; wherein said optical input means are for conveying said excitation light to said intrinsic optical sensing fiber means;

wherein said intrinsic optical sensing fiber means are for utilizing said excitation light to generate sensor modulated return light as a function of said sensed target objective;

wherein said optical return means are for conveying said sensor modulated return light away from said intrinsic optical sensing fiber means; wherein said intrinsic optical sensing fiber means comprises at least one intrinsic optical sensing fiber having an interface end face; wherein said optical return means comprise at least one return light optical fiber having an input end with an input end face defined by a taper; wherein said interface end face of said at least one intrinsic optical sensing fiber and said input end face of said at least one return light optical fiber at least substantially overlap with each other; and wherein said at least one return light optical fiber is tilted at an angle with respect to a longitudinal axis of said at least one intrinsic optical sensing fiber, such that said input end face of said at least one return light optical fiber is parallel to said interface end face of said at least one intrinsic optical sensing fiber, to tend to maximize the amount of said sensor modulated return light which is conveyed away from said at least one intrinsic optical sensing fiber by said least one return light optical fiber.

7. A multifunctional optical sensor system for sensing a sensed target objective, wherein said sensor system comprises:

an optical input means;

an intrinsic optical sensor means comprising an intrinsic optical sensing fiber means; and optical return means;

wherein said optical input means are adapted to receive excitation light from an excitation light source; wherein said optical input means are for conveying said excitation light to said intrinsic optical sensing fiber means;

wherein said intrinsic optical sensing fiber means are for utilizing said excitation light to generate sensor modulated return light as a function of said sensed target objective;

wherein said optical return means are for conveying said sensor modulated return light away from said intrinsic optical sensing fiber means; wherein said intrinsic optical sensing fiber means comprises at least one intrinsic optical sensing fiber having an interface end; wherein said optical return means comprise at least one return light optical fiber having an input end; wherein said interface end of said at least one intrinsic optical sensing fiber and said input end of said at least one return light optical fiber at least substantially overlap with each other; wherein said sensor modulated return light comprises sensor modulated fluorescence return light; wherein said at least one intrinsic optical sensing fiber has an external surface; wherein said intrinsic optical sensing fiber means further comprises at least one fluorophore on at least a portion of said external surface of said at least one intrinsic optical sensing fiber; wherein said at least one fluorophore emits said sensor modulated fluorescence return light as a function of said sensed target objective when said at least one fluorophore is in the presence of said sensed target objective and is simultaneously stimulated by said excitation light; wherein at least a majority of said sensor modulated fluorescence return light is concentrated in an interface annular ring extending over no more than about the outer 20% of said interface end of said at least one intrinsic optical sensing fiber; and wherein said input end of said at least one return light optical fiber at least substantially overlaps said interface annular ring, to tend to maximize the amount of said sensor modulated fluorescence return light which is conveyed away from said at least one intrinsic optical sensing fiber by said at least one return light optical fiber.

8. The multifunctional sensor system according to claim 7, wherein there are a plurality of said return light optical fibers; wherein each of said return light optical fibers has an input end; wherein said input ends of said plurality of return light optical fibers form an annular ring which at least substantially overlaps said interface annular ring of said interface end of said at least one intrinsic optical sensing fiber, to tend to maximize the amount of said sensor modulated fluorescence return light which is conveyed away from said at least one intrinsic optical sensing fiber by said plurality of return light optical fibers.

9. The multifunctional sensor system according to claim 8, wherein said optical input means comprises at least one excitation optical fiber having an output end; wherein said output end of said at least one excitation optical fiber is located at least substantially within said interface annular ring of said interface end of said at least one intrinsic optical sensing fiber; and wherein said output end of said at least one excitation optical fiber is located at least substantially within said annular ring formed by said input ends of said plurality of said return light optical fibers.

10. The multifunctional sensor system according to claim 8, wherein said annular ring formed by said input ends of said return light optical fibers is at least about 20% wider than said annular ring of said interface end of said at least one intrinsic optical sensing fiber, to tend to maximize the amount of said sensor modulated fluorescence return light which is conveyed away from said at least one intrinsic optical sensing fiber by said plurality of return light optical fibers, despite any lateral misalignment of said annular ring formed by said input ends of said return light optical fibers with respect to said annular ring of said interface end of said at least one intrinsic optical sensing fiber.

11. A multifunctional optical sensor system for sensing a sensed target objective, wherein said sensor system comprises:

an optical input means;

an intrinsic optical sensor means comprising an intrinsic optical sensing fiber means; and optical return means;

wherein said optical input means are adapted to receive excitation light from an excitation light source; wherein said optical input means are for conveying said excitation light to said intrinsic optical sensing fiber means;

wherein said intrinsic optical sensing fiber means are for utilizing said excitation light to generate sensor modulated return light as a function of said sensed target objective;

wherein said optical return means are for conveying said sensor modulated return light away from said intrinsic optical sensing fiber means; wherein said intrinsic optical sensing fiber means comprise at least one intrinsic optical sensing fiber and a diffuse scattering media; wherein said diffuse scattering media is located within at least a portion of said at least one intrinsic optical sensing fiber; wherein said sensor modulated return light comprises a first, sensor wave band of sensor modulated return light; wherein, in response to said excitation light, said intrinsic optical sensing fiber means also generates a second, reference wave band of return light; wherein said second reference wave band of return light comprises a backscattered portion of said excitation light that has been backscattered by said diffuse scattering media in the presence of said excitation light; wherein said sensor wave band of sensor modulated return light and said reference wave band of return light are not identical; and wherein said optical return means comprise ratiometric means for deriving a ratiometric electrical output signal from said sensor wave band of sensor modulated return light and from said reference wave band of return light, to tend to null certain optical errors in said multifunctional sensor system.

12. A multifunctional optical sensor system for sensing a sensed target objective, wherein said sensor system comprises:

an optical input means;

an intrinsic optical sensor means comprising an intrinsic optical sensing fiber means; and optical return means;

wherein said optical input means are adapted to receive excitation light from an excitation light source; wherein said optical input means are for conveying said excitation light to said intrinsic optical sensing fiber means;

wherein said intrinsic optical sensing fiber means are for utilizing said excitation light to generate sensor modulated return light as a function of said sensed target objective;

wherein said optical return means are for conveying said sensor modulated return light away from said intrinsic optical sensing fiber means; wherein said intrinsic optical sensing fiber means comprise at least one intrinsic optical sensing fiber having a sidewall; wherein said sidewall comprises a roughened portion; wherein said sensor modulated return light comprises a first, sensor wave band of sensor modulated return light; wherein, in response to said excitation light, said intrinsic optical sensing fiber means also generates a second, reference wave band of return light; wherein said second, reference wave band of return light comprises a backscattered portion of said excitation light that has been backscattered by said roughened portion of said sidewall of said at least one intrinsic optical sensing fiber; wherein said sensor wave band of sensor modulated return light and said reference wave band of return light are not identical; and wherein said optical return means comprise a ratiometric means for deriving a ratiometric electrical output signal from said sensor wave band of sensor modulated return light and from said reference wave band of return light, to tend to null certain optical errors in said multifunctional sensor system.

13. A multifunctional optical sensor system for sensing a sensed target objective, wherein said sensor system comprises:

an optical input means;

an intrinsic optical sensor means comprising an intrinsic optical sensing fiber means; and optical return means;

wherein said optical input means are adapted to receive excitation light from an excitation light source; wherein said optical input means are for conveying said excitation light to said intrinsic optical sensing fiber means;

wherein said intrinsic optical sensing fiber means are for utilizing said excitation light to generate sensor modulated return light as a function of said sensed target objective;

wherein said optical return means are for conveying said sensor modulated return light away from said intrinsic optical sensing fiber means; wherein said sensor modulated return light comprises a first, sensor wave band of sensor modulated return light; wherein, in response to said excitation light, said intrinsic optical sensing fiber means also generates a second, reference wave band of return light; wherein said sensor wave band of sensor modulated return light and said reference wave band of return light are not identical; wherein said optical return means comprise ratiometric means for deriving a ratiometric electrical output signal from said sensor wave band of sensor modulated return light and from said reference wave band of return light, to tend to null certain optical errors in said multifunctional sensor system; wherein said intrinsic optical sensing fiber means comprise at least a first fluorophore and a second fluorophore; wherein said first, sensor wave band of sensor modulated return light comprises fluorescence return light emitted by said first fluorophore when said first fluorophore is in the presence of said sensed target objective and is simultaneously stimulated by said excitation light; and wherein said second, reference wave band of return light comprises fluorescence return light emitted by said second fluorophore when said second fluorophore is stimulated by said excitation light.

14. A multifunctional optical sensor system for sensing a sensed target objective, wherein said sensor system comprises:

an optical input means;

an intrinsic optical sensor means comprising an intrinsic optical sensing fiber means; and optical return means;

wherein said optical input means are adapted to receive excitation light from an excitation light source; wherein said optical input means are for conveying said excitation light to said intrinsic optical sensing fiber means;

wherein said intrinsic optical sensing fiber means are for utilizing said excitation light to generate sensor modulated return light as a function of said sensed target objective;

wherein said optical return means are for conveying said sensor modulated return light away from said intrinsic optical sensing fiber means; wherein said intrinsic optical sensing fiber means comprises at least one intrinsic optical sensing fiber; wherein said intrinsic optical sensing fiber means further comprises an annular waveguide means; wherein said at least one intrinsic optical sensing fiber generates said sensor modulated return light; wherein said annular waveguide means at least partially surrounds said at least one intrinsic optical sensing fiber; and wherein said annular waveguide means are for capturing a captured portion of said sensor modulated return light generated by said at least one intrinsic optical sensing fiber, and are for delivering said captured portion of said sensor modulated return light to said optical return means.

15. The multifunctional sensor system according to claim 14, wherein said annular waveguide means has an outer surface, and wherein at least a portion of said outer surface is tapered with respect to a longitudinal axis of said annular waveguide means, to tend to decrease the angle at which said captured portion of said sensor modulated return light is injected by said annular waveguide means into said optical return means with respect to a longitudinal axis of an input portion of said optical return means.

16. The multifunctional sensor system according to claim 14, wherein said annular waveguide means has an inner surface; wherein said at least one intrinsic optical sensing fiber has an outer surface; and wherein a sensed target objective sampling chamber is at least partially defined between said inner surface of said annular waveguide means and said outer surface of said at least one intrinsic optical sensing fiber.

17. The multifunctional sensor system according to claim 14, wherein said annular waveguide means has an outer surface; and wherein at least a portion of said outer surface is mirrored, to tend to increase the amount of said captured portion of said sensor modulated return light and to tend to increase the amount of said captured portion of said sensor modulated return light which is delivered to said optical return means by said annular waveguide means.

18. The multifunctional sensor system according to claim 14, wherein said at least one intrinsic optical sensing fiber comprises a distal end; and wherein at least a portion of said distal end is mirrored, to tend to increase the amount of said sensor modulated return light which is generated by said at least one intrinsic optical sensing fiber.

19. The multifunctional sensor system according to claim 14, wherein said at least one intrinsic optical sensing fiber comprises a distal end; and wherein said distal end is tapered at an angle no greater than about 45°, to help prevent said excitation light from being reflected by said distal end.

20. The multifunctional sensor system according to claim 14, wherein said at least one intrinsic optical sensing fiber comprises a distal end; and wherein said distal end is at least partially covered with a material selected to absorb said excitation light, to help prevent said excitation light from being reflected by said distal end.

21. The multifunctional sensor system according to claim 14, wherein said annular waveguide means has an inner surface and an outer surface; wherein said at least one intrinsic optical sensing fiber has an outer surface; wherein at least a portion of said inner surface of said annular waveguide means is in contact with a corresponding portion of said outer surface of said at least one intrinsic optical sensing fiber; wherein at least a portion of said annular waveguide means is made from a material selected to permit said sensed target objective to pass through said annular waveguide means and reach at least part of said corresponding portion of said outer surface of said at least one intrinsic optical sensing fiber, when said outer surface of said annular waveguide means is exposed to said sensed target objective.

22. The multifunctional sensor system according to claim 21, wherein said outer surface of said at least one intrinsic optical sensing fiber comprises a layer of at least one fluorophore that is sensitive to said sensed target objective.

23. The multifunctional sensor system according to claim 14, wherein said annular waveguide means comprises an annular sensor optical fiber portion, an annular transition optical fiber portion, and an annular intrinsic optical sensing fiber portion which at least partially surrounds said at least one intrinsic optical sensing fiber; wherein said annular sensor optical fiber portion has a radial thickness greater than the radial thickness of said annular intrinsic optical sensing fiber portion which at least partially surrounds said at least one intrinsic optical sensing fiber; and wherein said annular transition optical fiber portion optically connects said annular sensor optical fiber portion and said annular intrinsic optical sensing fiber portion which at least partially surrounds said at least one intrinsic optical sensing fiber.

24. A multifunctional optical sensor system for sensing a sensed target objective, wherein said sensor system comprises:

an optical input means;

an intrinsic optical sensor means comprising an intrinsic optical sensing fiber means; and optical return means;

wherein said optical input means are adapted to receive excitation light from an excitation light source; wherein said optical input means are for conveying said excitation light to said intrinsic optical sensing fiber means;

wherein said intrinsic optical sensing fiber means are for utilizing said excitation light to generate sensor modulated return light as a function of said sensed target objective;

wherein said optical return means are for conveying said sensor modulated return light away from said intrinsic optical sensing fiber means; and wherein said intrinsic optical sensing fiber means comprises at least one sensor optical fiber in optical communication with at least one ribbon-like intrinsic optical sensing fiber.

25. The multifunctional sensor system according to claim 24, wherein said at least one sensor optical fiber has a thickness greater than the thickness of said at least one ribbon-like intrinsic optical sensing fiber; and wherein said intrinsic optical sensing fiber means further comprises a transition optical fiber means for optically connecting said at least one sensor optical fiber with said at least one ribbon-like intrinsic optical sensing fiber.

26. The multifunctional sensor system according to claim 25, wherein said at least one sensor optical fiber comprises at least one ribbon-like sensor optical fiber.

27. The multifunctional sensor system according to claim 25, wherein said at least one sensor optical fiber comprises a sidewall; and wherein at least a portion of said sidewall of said at least one sensor optical fiber is curved.

28. The multifunctional sensor system according to claim 24, wherein said at least one ribbon-like intrinsic optical sensing fiber comprises a distal end; and wherein said distal end is tapered at an angle of no greater than about 45°, to help prevent said excitation light from being reflected by said distal end.

29. The multifunctional sensor system according to claim 24, wherein said at least one ribbon-like intrinsic optical sensing fiber comprises a distal end; and wherein said distal end is at least partially covered with a material selected to absorb said excitation light, to help prevent said excitation light from being reflected by said distal end.

30. The multifunctional sensor system according to claim 24, wherein said at least one sensor optical fiber comprises at least one ribbon-like sensor optical fiber.

31. The multifunctional sensor system according to claim 24, wherein said at least one sensor optical fiber comprises a sidewall; and wherein at least a portion of said sidewall of said at least one sensor optical fiber is curved.

32. A multifunctional optical sensor system for sensing a sensed target objective, wherein said sensor system comprises:

an optical input means;

an intrinsic optical sensor means comprising an intrinsic optical sensing fiber means; and optical return means;

wherein said optical input means are adapted to receive excitation light from an excitation light source; wherein said optical input means are for conveying said excitation light to said intrinsic optical sensing fiber means;

wherein said intrinsic optical sensing fiber means are for utilizing said excitation light to generate sensor modulated return light as a function of said sensed target objective;

wherein said optical return means are for conveying said sensor modulated return light away from said intrinsic optical sensing fiber means; wherein said intrinsic optical sensing fiber means comprises at least one ribbon-like sensor optical fiber in optical communication with at least one ribbon-like intrinsic optical sensing fiber; wherein said optical input means comprises at least one excitation optical fiber having an output end; wherein said at least one ribbon-like sensor optical fiber has an interface end; wherein said optical return means comprises at least one return light optical fiber having an input end; and wherein said output end of said at least one excitation optical fiber and said input end of said at least one return light optical fiber are arranged to form a linear array which is located adjacent to said interface end of said at least one ribbon-like sensor optical fiber.

33. A multifunctional optical sensor system for sensing a sensed target objective, wherein said sensor system comprises:

an optical input means;

an intrinsic optical sensor means comprising an intrinsic optical sensing fiber means; and optical return means;

wherein said optical input means are adapted to receive excitation light from an excitation light source; wherein said optical input means are for conveying said excitation light to said intrinsic optical sensing fiber means;

wherein said intrinsic optical sensing fiber means are for utilizing said excitation light to generate sensor modulated return light as a function of said sensed target objective;

wherein said optical return means are for conveying said sensor modulated return light away from said intrinsic optical sensing fiber means; wherein said optical input means comprises at least one excitation optical fiber having an output end with a central portion; wherein said intrinsic optical sensing fiber means comprises at least one intrinsic optical sensing fiber having an interface end with a central portion; wherein said at least one excitation optical fiber is for conveying said excitation light to said at least one intrinsic optical sensing fiber; wherein said central portion of said output end of said at least one excitation optical fiber is at least generally coincident with said central portion of said interface end of said at least one intrinsic optical sensing fiber, to tend to maximize the amount of said excitation light which is conveyed by said at least one excitation optical fiber to said at least one intrinsic optical sensing fiber; wherein said optical return means comprise at least one return light optical fiber having an input end; wherein said at least one excitation optical fiber and said at least one return light optical fiber comprise separate optical fibers; and wherein said interface end of said at least one intrinsic optical sensing fiber and said input end of said at least one return light optical fiber at least substantially overlap with each other, to tend to maximize the amount of said sensor modulated return light which is conveyed away from said at least one intrinsic optical sensing fiber by said at least one return light optical fiber.

* * * * *